(12) United States Patent
Kshirsagar

(10) Patent No.: US 10,709,807 B2
(45) Date of Patent: Jul. 14, 2020

(54) POROUS DEVICES, KITS, AND METHODS FOR DEBRIDEMENT

(71) Applicant: 3M INNOVATIVE PROPERTIES COMPANY, St. Paul, MN (US)

(72) Inventor: Manjiri T. Kshirsagar, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 517 days.

(21) Appl. No.: 15/509,501

(22) PCT Filed: Sep. 28, 2015

(86) PCT No.: PCT/US2015/052563
§ 371 (c)(1),
(2) Date: Mar. 8, 2017

(87) PCT Pub. No.: WO2016/053829
PCT Pub. Date: Apr. 7, 2016

(65) Prior Publication Data
US 2017/0304485 A1 Oct. 26, 2017

Related U.S. Application Data

(60) Provisional application No. 62/058,208, filed on Oct. 1, 2014.

(51) Int. Cl.
*A61L 15/46* (2006.01)
*A61L 15/24* (2006.01)
(Continued)

(52) U.S. Cl.
CPC .............. *A61L 15/46* (2013.01); *A61B 90/80* (2016.02); *A61L 15/18* (2013.01); *A61L 15/24* (2013.01); *A61L 15/425* (2013.01)

(58) Field of Classification Search
CPC combination set(s) only.
See application file for complete search history.

(56) References Cited

U.S. PATENT DOCUMENTS

| 4,729,846 A | * | 3/1988 | Matsui | ................... C01G 49/06 252/62.56 |
| 5,498,478 A | * | 3/1996 | Hansen | ................. A61F 13/531 428/357 |

(Continued)

FOREIGN PATENT DOCUMENTS

| JP | 07-017816 | 1/1995 |
| JP | 2002-069897 | 3/2002 |

(Continued)

OTHER PUBLICATIONS

Debrisoft® Active Debridement, Patient Information Leaflet for the Use of Debrisoft® on Dry Skin and Wounds, Mar. 2012, 2 pages.

(Continued)

*Primary Examiner* — Tatyana Zalukaeva
*Assistant Examiner* — Guy K Townsend
(74) *Attorney, Agent, or Firm* — Andrian L. Pishko

(57) ABSTRACT

Porous devices are provided that include a particle-containing fibrous porous matrix and a fluid absorbed in the particle-containing porous fibrous nonwoven matrix. The particle-containing fibrous porous matrix includes a porous fibrous nonwoven matrix containing first polyolefin fibers, second polyolefin fibers including poly(ethylene), and fiberglass fibers; and microorganism-binding particles. The microorganism-binding particles are enmeshed in said porous fibrous nonwoven matrix. Methods of debridement are provided including providing a porous device including a particle-containing fibrous porous matrix and wiping a wound or an area of skin with the device; and providing a porous device including a porous fibrous nonwoven matrix and wiping a wound with the device. Further, kits are (Continued)

50μm provided including a sterile package containing at least one porous device, and typically also instructions for debridement.

14 Claims, 2 Drawing Sheets

(51) Int. Cl.
    *A61L 15/18*     (2006.01)
    *A61L 15/42*     (2006.01)
    *A61B 90/80*     (2016.01)

(56) References Cited

U.S. PATENT DOCUMENTS

| | | | | |
|---|---|---|---|---|
| 5,637,506 | A * | 6/1997 | Goken | B01J 20/28004 210/502.1 |
| 6,045,913 | A * | 4/2000 | Castle | B01J 2/16 428/403 |
| 7,214,847 | B1 * | 5/2007 | Flick | A61F 13/00008 428/103 |
| 2004/0049145 | A1 * | 3/2004 | Flick | A61F 13/104 602/41 |
| 2005/0244484 | A1 * | 11/2005 | Flick | A61N 1/0468 424/445 |
| 2007/0154510 | A1 * | 7/2007 | Wilcher | A61L 15/18 424/422 |
| 2008/0145455 | A1 * | 6/2008 | Bedard | A61K 33/06 424/682 |
| 2010/0131075 | A1 * | 5/2010 | Ludlow | A61L 27/3882 623/23.66 |
| 2010/0248214 | A1 * | 9/2010 | Kshirsagar | B01J 20/0229 435/5 |
| 2011/0250378 | A1 * | 10/2011 | Eaton | D04H 3/16 428/99 |
| 2011/0269179 | A1 * | 11/2011 | Kshirsagar | C12Q 1/04 435/34 |
| 2012/0046670 | A1 * | 2/2012 | Engl | A61F 13/00017 606/131 |
| 2013/0101805 | A1 * | 4/2013 | Altshuler | B32B 5/245 428/172 |
| 2013/0108831 | A1 * | 5/2013 | Wu | B32B 3/266 428/138 |
| 2013/0237114 | A1 | 9/2013 | Kawamoto | |
| 2013/0244225 | A1 * | 9/2013 | Kshirsagar | G01N 33/56911 435/5 |
| 2013/0260370 | A1 * | 10/2013 | Kshirsagar | G01N 1/405 435/5 |
| 2014/0194803 | A1 * | 7/2014 | Parks | A61K 33/42 602/48 |
| 2016/0206984 | A1 * | 7/2016 | Berrigan | D04H 3/02 |
| 2016/0220728 | A1 * | 8/2016 | Adams | A61K 8/0283 |
| 2017/0304485 | A1 * | 10/2017 | Kshirsagar | A61L 15/24 |
| 2018/0338945 | A1 * | 11/2018 | Sambasivam | A61P 31/04 |

FOREIGN PATENT DOCUMENTS

| | | | | |
|---|---|---|---|---|
| JP | 2012-107354 | | 6/2012 | |
| WO | 1992-007550 | | 4/1992 | |
| WO | 1999-027014 | | 6/1999 | |
| WO | 2009-046183 | | 4/2009 | |
| WO | 2009-046191 | | 4/2009 | |
| WO | 2010-085831 | | 8/2010 | |
| WO | 2012-078426 | | 6/2012 | |
| WO | 2013-016255 | | 1/2013 | |
| WO | 2013/184186 | | 12/2013 | |
| WO | WO20140194803 A1 * | 7/2014 | | A61L 26/00 |
| WO | 2014-200790 | | 12/2014 | |
| WO | 2015-047464 | | 4/2015 | |
| WO | 2015-095100 | | 6/2015 | |

OTHER PUBLICATIONS

International Search Report for PCT International Application No. PCT/US2015/052563, dated Dec. 17, 2015, 5 pGES.

* cited by examiner

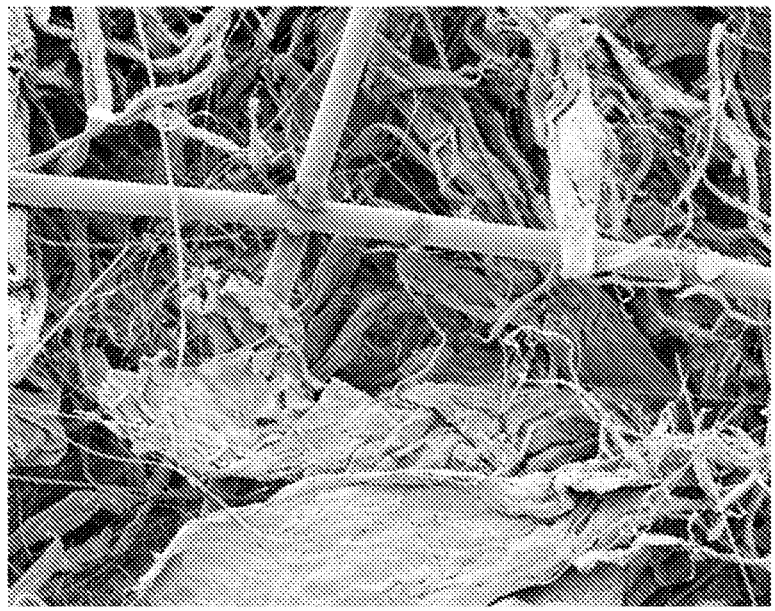
*Fig. 1*  50μm
*Fig. 2*  100μm

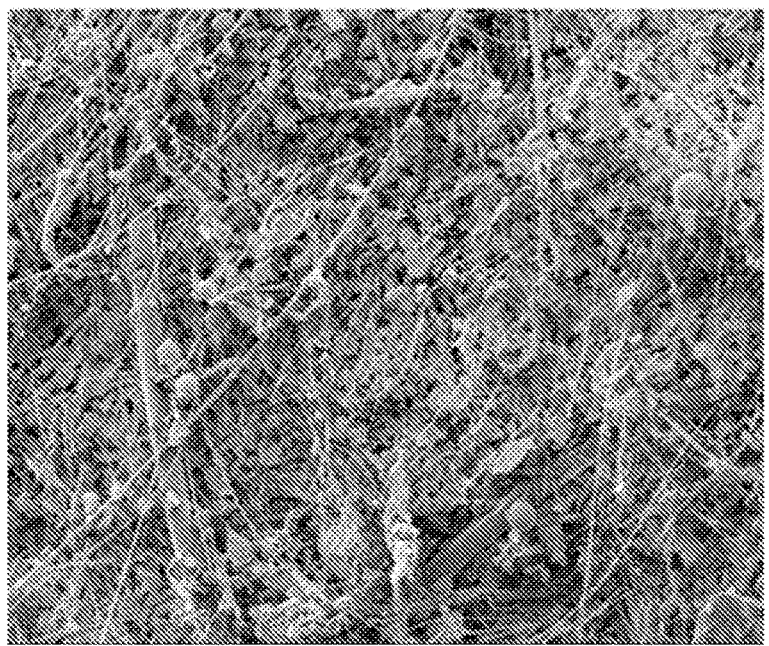
*Fig. 3*  100μm
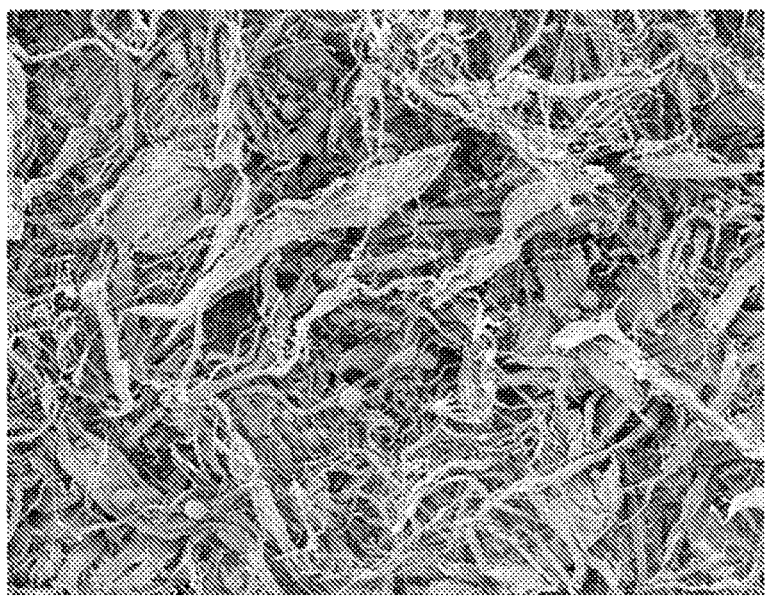
*Fig. 4*  200μm

POROUS DEVICES, KITS, AND METHODS FOR DEBRIDEMENT

CROSS REFERENCE TO RELATED APPLICATIONS

This application is a national stage filing under 35 U.S.C. 371 of PCT/US2015/052563, filed Sep. 28, 2015, which claims the benefit of U.S. application Ser. No. 62/058208, filed Oct. 1, 2014, the disclosure of which is incorporated by reference in its/their entirety herein.

FIELD

Porous devices, kits including the porous devices, and methods of making the porous devices are provided.

BACKGROUND

Wound cleaning/debriding is used to remove necrotic tissue, slough, microbial load (e.g., bacteria and biofilms), specifically in chronic, hard to heal wounds, in order to promote healing. Debridement has been performed by several methods, including physically by surgical procedures, chemically by debriding enzymes or lotions, and mechanically by negative pressure, water jets, and wipes. Each procedure has limitations; for instance, surgical debridement requires skilled medical personnel and tends to be an expensive lengthy, complicated procedure, of an invasive nature that removes healthy tissue as well. Chemical debridement options are limited by slow action as well as by cost. Similarly, mechanical options are expensive and require equipment as well as skilled personnel. These limitations restrict the number of in-home care options available to patients.

Thus, there is a need in the wound care area for a simple, relatively inexpensive and effective debridement method that can be performed in homes/clinics/institutions by caregivers to serve the chronic wound patients. There is also a need of a debridement option that can remove tissue gently as well as simultaneously remove bacteria.

SUMMARY

Porous devices are provided that include a fibrous porous matrix and microorganism-binding particles distributed throughout the fibrous porous matrix. The porous device can be used to debride a wound or dry skin.

In a first aspect, a porous device is provided. The device includes (a) a particle-containing porous fibrous nonwoven matrix including (i) a porous fibrous nonwoven and (ii) a plurality of microorganism-binding particles. The matrix includes first polyolefin fibers, second polyolefin fibers comprising poly(ethylene), and fiberglass fibers. The particles are enmeshed in the porous fibrous nonwoven matrix. The device further includes (b) a fluid absorbed in the particle-containing porous fibrous nonwoven matrix.

In a second aspect, a kit is provided. The kit includes (a) a sterile package and (b) at least one porous device according to the first aspect, disposed in the sterile package.

In a third aspect, a method of debridement is provided. The method includes (a) providing a porous device and (b) wiping a wound or an area of skin with the device. The porous device is according to the first aspect above.

In a fourth aspect, another method of debridement is provided. The method includes (a) providing a device including a porous fibrous nonwoven matrix and (b) wiping a wound with the device. The device includes a porous fibrous nonwoven matrix. The porous fibrous nonwoven matrix includes first polyolefin fibers, second polyolefin fibers comprising poly(ethylene), and fiberglass fibers.

In a fifth aspect, another kit is provided. The kit includes (a) a sterile package; (b) at least one device disposed in the sterile package; and (c) instructions for wiping a wound with the at least one device. The device includes (a) a porous fibrous nonwoven matrix including first polyolefin fibers, second polyolefin fibers comprising poly(ethylene), and fiberglass fibers. The device further includes (b) a fluid absorbed in the porous fibrous nonwoven matrix.

BRIEF DESCRIPTION OF THE DRAWINGS

FIG. 1 is the scanning electron micrograph (SEM) of the exemplary porous device of Example 1.

FIG. 2 is the SEM of the exemplary porous device of Example 2.

FIG. 3 is the SEM of the exemplary porous device of Example 9.

FIG. 4 is the SEM of the exemplary porous device of Example 55.

DETAILED DESCRIPTION

Porous devices are provided that include a fibrous porous matrix and microorganism-binding particles distributed in the fibrous porous matrix. The porous device can be included in a kit in which the porous device is disposed in a sterile package. The porous device can be used for debridement, such as to debride dry skin or a wound.

The term "a", "an", and "the" are used interchangeably with "at least one" to mean one or more of the elements being described.

The term "and/or" means either or both. For example "A and/or B" means only A, only B, or both A and B.

The term "enmeshed" (in regard to particles in a fibrous nonwoven matrix) means that the particles are entrapped in and on the fibrous nonwoven matrix (and, preferably, distributed within it), rather than solely being borne on its surface.

The term "fibrillated" (in regard to fibers or fibrous material) means treated (for example, by beating) in a manner that forms fibrils or branches attached to a fiber's main trunk.

The term "fibrous nonwoven matrix" means a web or medium, other than a woven or knitted fabric, comprising interlaid fibers (for example, a web comprising fibers that are interlaid by meltblowing, spunbonding, or other air laying techniques; carding; wet laying; or the like).

The term "fluid" means liquid, solution, or dispersion of solid or liquid in liquid.

The term "microorganism" means any cell or particle having genetic material suitable for analysis or detection (including, for example, bacteria, yeasts, viruses, and bacterial endospores).

The terms "polymer" and "polymeric material" are used interchangeably and refer to materials formed by reacting one or more monomers.

In a first aspect, a porous device is provided. The porous device includes (a) a particle-containing porous fibrous nonwoven matrix including (i) a porous fibrous nonwoven and (ii) a plurality of microorganism-binding particles. The matrix includes first polyolefin fibers, second polyolefin fibers comprising poly(ethylene), and fiberglass fibers. The particles are enmeshed in the porous fibrous nonwoven matrix. The device further includes (b) a fluid absorbed in the particle-containing porous fibrous nonwoven matrix. An advantage of the fibrous nonwoven matrix comprising at least three different types of fibers is that characteristics of the resulting device are tunable depending on the selection of specific fibers. For instance, texture (e.g., softness), structural integrity, and linting tendency can all be affected by the fiber selection and relative amounts.

The nonwoven, fibrous porous matrix is often in the form of a layer of interlaid fibers that are not woven or knitted together. The nonwoven, fibrous porous matrix can be prepared by any suitable process such as, for example, air laying techniques, spunlaid techniques such as meltblowing or spunbonding, carding, wetlaying, and combinations thereof. In some applications, it may be preferable to prepare the fibrous nonwoven matrix by spunlaid or wetlaid techniques.

The fluid absorbed in the particle-containing porous fibrous nonwoven matrix typically comprises water, a buffer solution, a cleansing solution, an analgesic solution, or an antimicrobial solution. Accordingly, the fluid may provide one or more benefits including moistening the dry skin or wound, removing contaminants with a cleanser (e.g., a surfactant), applying a pain reliever, applying a microorganism destroying agent, or a combination thereof. Typically, the fluid is present in an amount of at least 0.25 grams per gram of the particle-containing porous fibrous nonwoven matrix, or at least 0.5 grams per gram, or at least 0.75 grams per gram, or at least 1.0 grams per gram, or at least 1.5 grams per gram, or at least 2.0 grams per gram of the particle-containing porous fibrous nonwoven matrix. In an embodiment, the fluid is present in an amount such that the particle-containing porous fibrous nonwoven matrix is saturated, wherein the matrix holds as much fluid as can be absorbed. A saturated particle-containing porous fibrous nonwoven matrix may be particularly useful for wiping dry skin, for instance. Alternatively, the fluid can be present in an amount of up to 8.0 grams per gram of the particle-containing porous fibrous nonwoven matrix, or up to 6.0 grams per gram, or up to 5.0 grams per gram, or up to 4.0 grams per gram, or up to 3.0 grams per gram, or up to 2.5 grams per gram of the particle-containing porous fibrous nonwoven matrix. In an embodiment, the particle-containing porous fibrous nonwoven matrix is not saturated, such that the matrix has the capacity to absorb wound exudates. In certain embodiments, the fluid is present in an amount from 0.25 to 5.0 grams per gram of the particle-containing porous fibrous nonwoven matrix, or in an amount from 0.5 to 4.0 grams per gram, or in an amount from 0.25 to 1.0 grams per gram, or in an amount from 1.5 to 5.0 grams per gram, or in an amount from 2.0 to 8.0 grams per gram of the particle-containing porous fibrous nonwoven matrix.

Fibers suitable for use in preparing the nonwoven, fibrous porous matrix are usually pulpable or extrudable fibers such as those that are stable to radiation and/or to a variety of solvents. Optionally, at least some of the polymeric fibers can be selected to exhibit a degree of hydrophilicity. Useful fibers include polymeric fibers, inorganic fibers, and combinations thereof. More particularly, the fibers include a plurality of different types of polymeric fibers, including first polyolefin fibers, second polyolefin fibers comprising poly(ethylene), and fiberglass fibers. In an embodiment, the first polyolefin fibers comprise poly(ethylene), where the poly(ethylene) of the first polyolefin fibers is different from the poly(ethylene) of the second polyolefin fibers. Additional suitable fibers include for example and without limitation, nylon fibers and polylactic acid fibers.

Suitable polymeric fibers include those made from natural polymers (those derived from animal or vegetable sources) and/or synthetic polymers, including thermoplastic and solvent-dispersible polymers. Useful polymers include poly-lactic acid, polyolefins (for example, poly(ethylene) (e.g., low density polyethylene, medium density polyethylene, high density polyethylene, etc.), polypropylene, poly(1-butene), copolymers of ethylene and propylene, alpha olefin copolymers such as copolymers of ethylene or propylene with 1-butene, 1-hexene, 1-octene, and 1-decene such as poly(ethylene-co-1-butene), poly(ethylene-co-1-butene-co-1-hexene), and the like); poly(isoprenes); poly(butadienes); polyamides (for example, nylon 6, nylon 6,6, nylon 6,12, poly(iminoadipoyliminohexamethylene), poly(iminoadi-poyliminodecamethylene), polycaprolactam, and the like); polyimides (for example, poly(pyromellitimide) and the like); polyethers; poly(ether sulfones) (for example, poly(diphenylether sulfone), poly(diphenylsulfone-co-diphenylene oxide sulfone), and the like); poly(sulfones); poly(vinyl esters) such as poly(vinyl acetates); copolymers of vinyl acetate (for example, poly(ethylene-co-vinyl acetate), copolymers in which at least some of the acetate groups have been hydrolyzed to provide various poly(vinyl alcohols) including poly(ethylene-co-vinyl alcohol), and the like); poly(phosphazenes); poly(vinyl ethers); poly(vinyl alcohols); polyaramids (for example, para-aramids such as poly(paraphenylene terephthalamide) and fibers sold under the trade designation "KEVLAR" by DuPont Co., Wilmington, Del., pulps of which are commercially available in various grades based on the length of the fibers that make up the pulp such as, for example, "KEVLAR 1F306" and "KEVLAR 1F694", both of which include aramid fibers that are at least 4 mm in length; and the like); wool; silk; cellulosic polymers (for example, cellulose, cellulose derivatives such as rayon, and the like); fluorinated polymers (for example, poly(vinyl fluoride), poly(vinylidene fluoride), copolymers of vinylidene fluoride such as poly(vinylidene fluoride-co-hexafluoropropylene), copolymers of chlorotrifluoroethylene such as poly(ethylene-co-chlorotrifluoroethylene), and the like); chlorinated polymers; poly(carbonates); and the like; and combinations thereof.

Suitable inorganic fibers include those that contain at least one inorganic material selected from glasses, ceramics, and combinations thereof. These fibers are often added to provide strength to the fibrous porous matrix. For example, porous matrix layers containing inorganic fibers are often capable of being bent, folded, or pleated without breaking apart. Useful inorganic fibers include, for example, fiberglass (for example, E-glass, S-glass, and the like), ceramic fibers (for example, fibers made of metal oxides (such as alumina), silicon carbide, boron nitride, boron carbide, and the like), and combinations thereof. Useful ceramic fibers can be at least partially crystalline (exhibiting a discernible X-ray powder diffraction pattern or containing both crystalline and amorphous (glass) phases). In some applications, the inorganic fibers include fiberglass and combinations thereof.

In some embodiments, mixtures of hydrophobic and hydrophilic polymeric fibers are used. For example, the fibrous porous matrix can include a mixture of hydrophobic fibers such as polyolefins plus hydrophilic fibers such as polyamides and polysulfones. In some specific examples, the polymeric fibers include polyamides, polyolefins, and fiberglass.

The fibers used to form the nonwoven fibrous porous matrix can be of a length and diameter that can provide a porous matrix having sufficient structural integrity and sufficient porosity for a particular application (for example, wound debridement). The fiber lengths are often at least about 0.5 millimeter, at least 1 millimeter, at least 2 millimeters, at least 3 millimeters, at least 4 millimeters, at least 6 millimeters, at least 8 millimeters, at least 10 millimeters, at least 15 millimeters, at least 20 millimeters, at least 25 millimeters, or at least 30 millimeters. The diameter of the fibers can be, for example, at least 10 micrometers, at least 20 micrometers, at least 40 micrometers, or at least 60 micrometers. The fiber lengths and diameters will vary depending upon factors such as the nature of the fiber and the type of application.

To facilitate entrapment of the microorganism-binding particles and/or to ensure a high surface area, the fibers used to form the nonwoven, fibrous porous matrix often contain at least one fibrillated fiber (for example, in the form of a main fiber surrounded by many smaller attached fibrils). The main fiber generally can have a length in the range of 0.5 millimeters to 5 millimeters and a diameter in a range of 1 micrometer to 20 micrometers. The fibrils typically can have a sub-micrometer diameter. In many embodiments, the fibrillated fibers are prepared from a polyolefin such as poly(ethylene) or polypropylene.

The nonwoven, fibrous porous matrix contains a plurality of different types of fibers. In some embodiments, the porous matrix can be formed using three, four, or even more different types of fibers. For example, a nylon fiber can be added for strength and integrity, while fibrillated poly(ethylene) can be added for entrapment of the particulates. Additionally, nylon fibers provide hydrophilic character while fibrillated poly(ethylene) fibers provide hydrophobic character to the porous matrix. If fibrillated and non-fibrillated fibers are used in combination, the weight ratio of fibrillated fibers to non-fibrillated fibers is often at least 1:2, at least 1:1, at least 2:1, at least 3:1, at least 5:1, or even at least 8:1.

The nonwoven, fibrous porous matrix further contains at least one polymeric binder. Suitable polymeric binders include natural and synthetic polymeric materials that are relatively inert (exhibiting little or no chemical interaction with either the fibers or the microorganism-binding particles). Useful polymeric binders include polymeric binder fibers. For some applications, useful polymeric binders include polymeric resins (for example, in the form of powders and latexes). Typically, the use of larger amounts of the polymeric binder results in decreased linting of the device.

Suitable polymeric binder fibers include adhesive-only type fibers and bi-component fibers. Bi-component fibers can have, for example, a core-sheath structure, a side-by-side structure, an islands-in-the-sea structure, or a segmented-pie structure, or the like. An example side-by-side bi-component fiber is the polyolefin thermally bonded bi-component fiber that is commercially available from Chisso Corporation (Osaka, Japan) under the trade designation CHISSO (for example, CHISSO ES). An example core-sheath bi-component fiber is commercially available from Unitika Ltd. (Osaka, Japan) under the trade designation MELTY (for example, MELTY 4080) and those commercially available from Minifibers, Inc. (Johnson City, Tenn.) made of ethyl vinyl acetate (sheath) and polypropylene (core). The binder is the sheath portion of the sheath-core bi-component fiber. Suitable polymeric resins for the polymeric binder can include, but are not limited to, natural rubbers, neoprene, styrene-butadiene copolymers, acrylate resins, polyvinyl chloride, polyvinyl acetate, and the like, and combinations thereof.

The amount of binder in the resulting porous fibrous matrix (in dry form) can be from about 3 weight percent to about 7 weight percent including about 5 weight percent, based upon the total weight of all components of the porous fibrous matrix. Such amounts of polymeric binder generally can provide the nonwoven, porous fibrous matrix with sufficient integrity for use in many applications, while not significantly coating the microorganism-binding particles. Surprisingly, the amount of polymeric binder in the nonwoven, porous fibrous matrix can be less than about 5, 4, 3, 2, or even 1 percent by weight, relative to the weight of the fibers in the nonwoven, porous fibrous matrix.

The nonwoven, fibrous porous matrix often includes a mixture of polyolefin fibers, polyamide fibers, glass fibers, and polymeric binder. In some particular embodiments, the nonwoven, fibrous porous matrix contains a mixture of nylon fibers, fibrillated polyethylene fibers, glass fibers, and polymeric binder fibers (e.g. sheath-core bi-component fiber). In some examples, the nonwoven, fibrous porous matrix contains 40 to 80 weight percent fibrillated polyethylene fibers, 10 to 30 weight percent nylon fibers, 5 to 20 weight percent glass fibers, and 5 to 20 weight percent polymer binder fibers. In other examples, the nonwoven, fibrous porous matrix contains 50 to 70 weight percent fibrillated polyethylene fibers, 10 to 25 weight percent nylon fibers, 5 to 15 weight percent glass fibers, and 5 to 20 weight percent polymeric binder fibers. In still other examples, the fibrous porous matrix contains 55 to 65 weight percent fibrillated polyethylene fibers, 10 to 20 weight percent nylon fibers, 5 to 15 weight percent glass fibers, and 10 to 20 weight percent polymeric binder fibers.

In many embodiments, the fibrous porous matrix contains only fibers. For example, at least 90 weight percent, at least 95 weight percent, at least 98 weight percent, at least 99 weight percent, or at least 99.5 weight percent of a dry fibrous porous matrix is fibers.

The porous device typically includes both the fibrous porous matrix and microorganism-binding particles distributed within the fibrous porous matrix. In most embodiments, the porous device contains at least 10 weight percent microorganism-binding particles based on a total dry weight of the porous device. If the amount of the microorganism-binding particles is lower than about 10 weight percent, the porous device may not contain enough microorganism-binding particles to effectively capture microorganisms removed from a wound bed or skin. In some examples, the porous device contains at least 15 weight percent, at least 20 weight percent, at least 25 weight percent, or at least 30 weight percent microorganism-binding particles based on a total dry weight of the porous device.

On the other hand, the porous device usually contains no greater than 55 weight percent microorganism-binding particles based on the total dry weight of the porous device. If the amount of the microorganism-binding particles is greater than about 55 weight percent, the porous device may contain an insufficient amount of the fibrous porous matrix. That is, the strength of the porous device may be insufficient to hold together when employed as a wipe. In some examples, the porous device contains no greater than 50 weight percent, no greater than 45 weight percent, or no greater than 40 weight percent microorganism-binding particles based on a total weight of the porous device.

Stated differently, the porous device often contains 10 to 55 weight percent microorganism-binding particles and 45 to 90 weight percent fibrous porous matrix, 15 to 50 weight percent microorganism-binding particles and 50 to 85 weight percent fibrous porous matrix, 20 to 50 weight percent microorganism-binding particles and 50 to 80 weight percent fibrous porous matrix, 20 to 45 weight percent microorganism-binding particles and 55 to 80 weight percent fibrous porous matrix, 25 to 40 weight percent microorganism-binding particles and 60 to 75 weight percent fibrous porous matrix, or 30 to 40 weight percent microorganism-binding particles and 60 to 70 weight percent fibrous porous matrix. The amounts are based on the total dry weight of the porous device.

In many embodiments, the porous device (when dry) contains only microorganism-binding particles and fibrous porous matrix. For example, the porous device contains at least 90 weight percent, at least 95 weight percent, at least 98 weight percent, at least 99 weight percent, or at least 99.5 weight percent combined microorganism-binding particles and fibrous porous matrix when dry.

Microorganism-binding particles are water-insoluble particulate materials that have been employed to non-specifically capture microorganisms when contacted with fluid samples containing microorganisms. The microorganism-binding particles typically comprise particles selected from the group consisting of amorphous metal silicates, guanidine-functionalized metal silicates, diatomaceous earth, surface-modified diatomaceous earth, gamma-FeO(OH), metal carbonates, metal phosphates, silica, and combinations thereof. The microorganism-binding particles typically comprise microparticles.

In an embodiment, the microorganism-binding particles comprise particles of amorphous, spheroidized metal silicates, such as amorphous, spheroidized magnesium silicate, amorphous, spheroidized aluminum silicate, or a combination thereof. Amorphous, at least partially fused particulate forms of metal silicate can be prepared by any of the known methods of melting or softening relatively small feed particles (for example, average particle sizes up to about 25 micrometers) under controlled conditions to make generally ellipsoidal or spheroidal particles (that is, particles having magnified two-dimensional images that are generally rounded and free of sharp corners or edges, including truly or substantially circular and elliptical shapes and any other rounded or curved shapes). Such methods include atomization, fire polishing, direct fusion, and the like. A preferred method is flame fusion, in which at least partially fused, substantially glassy particles are formed by direct fusion or fire polishing of solid feed particles (for example, as in the method described in U.S. Pat. No. 6,045,913 (Castle et al.). Most preferably, such methods can be utilized to produce amorphous, spheroidized metal silicates by converting a substantial portion of irregularly-shaped feed particles (for example, from about 15 to about 99 volume percent; preferably, from about 50 to about 99 volume percent; more preferably, from about 75 to about 99 volume percent; most preferably, from about 90 to about 99 volume percent) to generally ellipsoidal or spheroidal particles.

Some amorphous metal silicates are commercially available. For example, amorphous, spheroidized magnesium silicate is commercially available for use in cosmetic formulations (for example, "3M COSMETIC MICROSPHERES CM-111", available from 3M Company, St. Paul, Minn.). 3M COSMETIC MICROSPHERES CM-111 have a particle density of 2.3 g/cc, a surface area of 3.3 m$^2$/g, and have a particle size of: 90 percent less than 11 microns (i.e., $D_{90}$=11), 50 percent less than 5 microns, and 10 percent less than 2 microns. Amorphous aluminum silicate is commercially available for use in paints, primers, powder coatings, and other coatings, for example, "3M CERAMIC MICROSPHERES" from 3M Company, St. Paul, Minn. The 3M CERAMIC MICROSPHERES are alkali alumino silicate ceramic microspheres shaped as solid spheres with particle density of 2.4 g/cc, and are commercially available in three grades: W-210, W-410, and W0610. W-210 particles have a surface area of 5 m$^2$/cc and a particle size of: 95 percent less than about 12 microns (i.e., $D_{95}$=12), 90 percent less than about 9 microns, 50 percent less than about 3 microns, and 10 percent less than about 1 micron. W-410 particles have a surface area of 3 m$^2$/cc and a particle size of: 95 percent less than about 24 microns (i.e., $D_{95}$=24), 90 percent less than about 15 microns, 50 percent less than about 4 microns, and 10 percent less than about 1 micron. W-610 particles have a surface area of 3 m$^2$/cc and a particle size of: 95 percent less than about 40 microns (i.e., $D_{95}$=40), 90 percent less than about 28 microns, 50 percent less than about 10 microns, and 10 percent less than about 1 micron.

In certain embodiments, the particles are guanidine-functionalized metal silicate particles. A guanidine-functionalized particle can be made, for example, according to methods disclosed in commonly assigned International Application No. PCT/US2014/040861 (Kshirsagar et al.). A guanidine-functionalized metal silicate particle comprises at least one guanidine-containing ligand. The guanidine-containing ligand is formed by modifying the metal silicate particle with a guanidine-containing silane having the structure shown in Formula 1:

$$X_{3-n}R^a{}_nSi\text{—}Y\text{-}G \qquad \text{Formula 1}$$

In Formula 1, Si is a silicon atom, and G denotes a guanidine group of the formula —NH—C(=NH)—NH$_2$. Y is a divalent group that is covalently bonded to the silicon atom at one end and to the G group at the other end. Each R$^a$ group, if any are present, is independently an alkyl, aralkyl, or aryl group, and is attached to the silicon atom. Each X is a leaving group covalently bonded to the silicon atom and is independently alkoxy or acyloxy, and n is 0, 1, or 2. A typical alkylene can be up to 20, up to 16, 12, 10, 8, 7, 6, 5, 4, or even up to 3 carbons, or even 2 carbons, inclusive of the terminal atoms of the divalent group. In some embodiments, Y is a divalent group comprising an alkylene of 3 to 6 carbons. In a preferred embodiment, Y is a divalent group having 3 carbons (i.e., propyl).

In Formula 1, each leaving group X is independently an alkoxy group of 1, 2, 3, 4, 5, 6, 7, 8, 9, or even up to 10 carbons, or is an acyloxy group of 2 carbons, or 3, 4, 5, 6, 7, 8, 9, or even up to 10 carbons, where the alkoxy or acyloxy group is bonded to the silicon through an oxygen atom.

In some embodiments, n is 0. When n is 0, no R$^a$ groups are present, and Formula 1 can be re-written more simply as shown in Formula 2 (where Si, G, Y, and X are as defined for Formula 1):

$$X_3Si\text{—}Y\text{-}G \qquad \text{Formula 2}$$

When the silane of Formula 1 (or Formula 2) reacts with an —OH group on the surface of a metal silicate particle, at least one X leaving group is replaced by a covalent bond of between the silicon atom and an oxygen atom on the surface of the metal silicate particle. An embodiment of a guanidine-functionalized metal silicate particle comprising a specific exemplary guanidine-containing ligand within the general type represented by Formula 1, wherein n=0 (i.e., as in Formula 2), is shown in Formula 3 (the circle in Formula 3 represents a metal silicate particle):

Formula 3

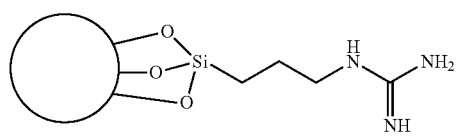

It will be understood that Formula 3 represents a specific embodiment wherein n is 3 and Y is a divalent group that is alkylene having 3 carbons. In each of Formulas 1 to 3, the ionization state of the guanidine group is omitted; however, it will be understood that in various environments such guanidine groups may be charged or uncharged (e.g., protonated or deprotonated), for example, according to the pH of a liquid medium in which the guanidine group is present.

The covalent bond(s) between the oxygen(s) of the ligand and the particle can be conveniently obtained, for example, by reacting a Si-bonded hydrolyzable group of the guanidine-containing precursor with a hydroxyl group of the particle. While the exemplary structure of Formula 3 shows three such bonded oxygen atoms (i.e., n=3 in Formula 1), it will be appreciated that in various embodiments one, two or three such bonded oxygen atoms can be provided. If less than three such oxygen atoms are bonded to the silicon atom, other substituents (e.g., substituents that are not bonded to the particle, and which are not shown in Formula 1) may be present on the silicon atom. For example, the guanidine-containing ligand can include a polymeric structure involving formation of Si—O—Si (i.e., siloxane) groups, resulting from Si—O bonds being formed between two or more guanidine-containing ligand precursors. Without being bound by theory, it is thought that Si—O—Si groups may form in the presence of added water, or other aqueous solvents, or other agent that can hydrolyze bonds in Si—O—R groups, to give rise to more complex guanidine-containing ligand structures attached to particles.

A network of polymerized guanidine-containing ligands can form a coating on the surface of the metal silicate particle. In some embodiments it may be desirable to obtain the particle functionalized with polymerized guanidine-containing ligand (e.g., having at least one Si—O—Si group in the polymerized guanidine-containing ligand), as a means of increasing the loading of nitrogen-containing guanidine groups on the surface of the metal silicate particle. It is thought that in at least these types of polymerizations, a loading of nitrogen-containing guanidine groups on the surface of the metal silicate particle can attain levels of surface nitrogen content in a range from 1 to 10 atomic percent, as can be measured, for example, by X-ray photoelectron spectroscopy.

Guanidine-functionalized particles of the present disclosure include metal silicate particles. Useful metal silicates include silicates of metals such as magnesium, calcium, zinc, aluminum, iron, titanium, and the like (preferably, magnesium and aluminum), and combinations thereof. Preferred are amorphous metal silicates in at least partially fused particulate form. In certain embodiments, more preferred are amorphous, spheroidized metal silicates; and even more preferably, amorphous, spheroidized magnesium silicate. In certain embodiments, more preferred are amorphous aluminum silicates. Metal silicates are known and can be chemically synthesized by known methods or obtained through the mining and processing of raw ores that are naturally-occurring.

The metal silicate particle, such as a magnesium silicate particle, bears sufficient surface hydroxyl groups (typically, Si—OH groups) to enable a desired number of guanidine-containing ligands to be covalently attached thereto.

The guanidine-functionalized metal silicate particles used in porous devices of the present disclosure can be used in essentially any particulate form (preferably, a relatively dry or volatiles-free form) that is amenable to blending with fibers to form the porous devices of the present disclosure. Preferably, the guanidine-functionalized metal particles are used in the form of a powder. Useful powders include those that comprise microparticles (preferably, microparticles having a particle size in the range of about 1 micrometer (more preferably, about 2 micrometers; even more preferably, about 3 micrometers; most preferably, about 4 micrometers) to about 100 micrometers (more preferably, about 50 micrometers; even more preferably, about 25 micrometers; most preferably, about 15 or 20 micrometers; where any lower limit can be paired with any upper limit of the range, as referenced above).

In some embodiments, particularly preferred are guanidine-functionalized magnesium silicate particles. Suitable guanidine-functionalized magnesium silicate particles for use in carrying out the process of the present disclosure include those that comprise an amorphous magnesium silicate and that have a surface composition having a metal atom to silicon atom ratio greater than 0.01 and less than or equal to about 0.5 (preferably, less than or equal to about 0.4; more preferably, less than or equal to about 0.3; most preferably, less than or equal to about 0.2), as determined by X-ray photoelectron spectroscopy ("XPS", also known as Electron Spectroscopy for Chemical Analysis ("ESCA")). In some embodiments, particularly preferred are guanidine-functionalized aluminum silicate particles. Suitable guanidine-functionalized aluminum silicate particles for use in carrying out the process of the present disclosure include those that comprise an amorphous aluminum silicate and that have a surface composition having a metal atom to silicon atom ratio greater than 6.7 and less than or equal to about 17.3, as determined by XPS (also known as ESCA).

XPS is a technique that can provide information about the elemental and chemical (oxidation state and/or functional group) concentrations present on a solid surface. XPS typically provides an analysis of the outermost 3 to 10 nanometers (nm) of the specimen surface. XPS is sensitive to all elements in the periodic table except hydrogen and helium with detection limits for most species in the 0.1 to 1 atomic percent concentration range. In some cases, for example for CM-111 particles, a preferred surface composition assessment conditions for XPS can include a take-off angle of 90 degrees measured with respect to the sample surface with a solid angle of acceptance of ±10 degrees. A person skilled in the art can select a suitable instrument setting for analysis of particles of the present disclosure.

In embodiments of the present disclosure, guanidine-functionalized metal silicate particles have a surface nitrogen content in a range from 1 atomic percent to 20 atomic percent, as measured by XPS. In some embodiments, the guanidine-functionalized metal silicate particles have a surface nitrogen content of at least 1 atomic percent, at least 2, at least 3, at least 4, or even at least 5 atomic percent, as measured by XPS. In some embodiments, the guanidine-functionalized metal silicate particles have a surface nitrogen content of up to 20 atomic percent, up to 15, up to 10, up to 9, up to 8, up to 7, or even up to 6 atomic percent, as measured by XPS. The surface nitrogen content of the guanidine-functionalized metal silicate particles, as measured by XPS, may be any combination of these lower and upper values, inclusive of the values thereof. A person skilled in the art would understand that in some embodiments it may be preferred to select higher or lower surface nitrogen content within these ranges, depending on the desired application.

In an embodiment, the microorganism-binding particles comprise particles of diatomaceous earth, for instance particles of surface-modified diatomaceous earth. Diatomaceous earth (or kieselguhr) is a natural siliceous material produced from the remnants of diatoms, a class of ocean-dwelling microorganisms. Thus, it can be obtained from natural sources and is also commercially available (for example, from Alfa Aesar, A Johnson Matthey Company, Ward Hill, Mass.). Diatomaceous earth particles generally comprise small, open networks of silica in the form of symmetrical cubes, cylinders, spheres, plates, rectangular boxes, and the like. The pore structures in these particles can generally be remarkably uniform.

Diatomaceous earth can be used in carrying out the process of the invention as the raw, mined material or as purified and optionally milled particles. Preferably, the diatomaceous earth is in the form of milled particles with sizes in the range of about 1 micrometer to about 50 micrometers in diameter (more preferably, about 3 micrometers to about 10 micrometers). The diatomaceous earth can optionally be heat treated prior to use to remove any vestiges of organic residues. If a heat treatment is used, it can be preferable that the heat treatment be at 500° C. or lower, as higher temperatures can produce undesirably high levels of crystalline silica.

Surface-modified diatomaceous earth comprises diatomaceous earth bearing, on at least a portion of its surface, a surface treatment comprising titanium dioxide, ferric oxide, fine-nanoscale gold or platinum, or a combination thereof. Useful surface modifiers include fine-nanoscale gold; fine-nanoscale platinum; fine-nanoscale gold in combination with at least one metal oxide (preferably, titanium dioxide, ferric oxide, or a combination thereof); titanium dioxide; titanium dioxide in combination with at least one other (that is, other than titanium dioxide) metal oxide; and the like; and combinations thereof. Preferred surface modifiers include fine-nanoscale gold; fine-nanoscale platinum; fine-nanoscale gold in combination with at least ferric oxide or titanium dioxide; titanium dioxide; titanium dioxide in combination with at least ferric oxide; and combinations thereof. Surface-modified diatomaceous earth can be made, for example, according to methods disclosed in commonly assigned International Publication No. WO 2009/046191 (Kshirsagar et al.).

In an embodiment, the microorganism-binding particles comprise particles of gamma-FeO(OH) (also known as lepidocrocite). Specific examples of such microorganism-binding particles are disclosed in commonly assigned International Publication No. WO2009/046183 (Kshirsagar et al.). Gamma-FeO(OH) particles have been found to be surprisingly more effective than other iron-containing microorganism-binding particles in capturing gram-negative bacteria, which can be of great concern in regard to human bacterial infections.

Gamma-FeO(OH) is known and can be chemically synthesized by known methods (for example, by oxidation of ferrous hydroxide at neutral or slightly acidic pHs, as described for purposes of magnetic tape production in U.S. Pat. No. 4,729,846 (Matsui et al.), the description of which is incorporated herein by reference). Gamma-FeO(OH) is also commercially available (for example, from Alfa Aesar, A Johnson Matthey Company, Ward Hill, Mass., and from Sigma-Aldrich Corporation, St. Louis, Mo.).

In an embodiment, the microorganism-binding particles comprise particles of silica. A specific example of microorganism-binding silica particles is silicon dioxide microspheres having a mean diameter of about 2.5 microns that are commercially available from PolySciences, Inc., (Warrington, Pa.).

In an embodiment, the microorganism-binding particles comprise particles of metal carbonates. A specific example of microorganism-binding metal carbonate particles is calcium carbonate, such as calcium carbonate particles having a diameter range of 2.5-10 microns that are commercially available from Sigma-Aldrich, (St. Louis, Mo.).

In an embodiment, the microorganism-binding particles comprise particles of metal phosphates. A specific example of microorganism-binding metal phosphate particles is hydroxyapatite, such type-1 hydroxyapatite particles having particle sizes from 2-8 microns that are commercially available from Sigma-Aldrich, (St. Louis, Mo.).

In one specific method, the porous device is prepared using a wet laying or "wetlaid" process. In this process, a dispersion is formed that contains (a) a plurality of fibers, (b) a plurality of microorganism-binding particles, (c) polymeric binder fibers, (d) and a dispersing liquid such as water, a water-miscible organic solvent, or a mixture thereof. The fibers, microorganism-binding particles, and polymeric binder fiber components can be dispersed together in the dispersing liquid. Alternatively, one or two of these components can be dispersed prior to the introduction of the other components. In some embodiments, the fibers (for example, hydrophobic fibers) have additives, surface treatments, or chemical groups that facilitate dispersion of the fibers in the dispersion liquid. For example, polyolefin-based fibers can have maleic anhydride or succinic anhydride functionality, or, during the melt-processing to prepare polyolefin-based fibers, a suitable surfactant can be added.

The wetlaid process additionally includes dewatering, followed by heating to finish the dewatering and to melt the polymeric binder fibers (and thereby deposit polymeric binder on the fibers).

One or more adjuvants or additives can be used in preparing this type of porous device. Useful adjuvants include process aids (for example, precipitation agents such as sodium aluminates and aluminum sulfate, which can aid in precipitating the polymeric binder onto the fibers), materials that can enhance the overall performance of the resulting porous device, and the like. When used, the amounts of such adjuvants can be present, for example, in an amount up 5 weight percent, up to 4 weight percent, up to 3 weight percent, up to 1 weight percent, or up to 0.5 weight percent based on a total dry weight of the porous device (for example, fibers and microorganism-binding particles). The total amount of adjuvants is typically selected to be as low as possible so as to maximize the amount of microorganism-binding particles that can be included in the porous device.

In one more specific wetlaid process, the fibers (for example, chopped fibers) can be blended in a container in the presence of the dispersing liquid (for example, water, a water-miscible organic solvent such as an alcohol, or a mixture thereof) to form a slurry. After formation of the slurry, the microorganism-binding particles and an optional precipitation agent (for example, a pH adjusting agent such as alum) can be added to the slurry.

When the wetlaid process is carried out by using hand-sheet methods known in the art, the order of addition of the components (i.e., fibers and microorganism-binding particles) to the dispersion has not been found to significantly affect the ultimate performance of the concentration device. After formation, the dispersion mixture can be poured into a mold, the bottom of which can be covered by a screen. The dispersing liquid can be allowed to drain from the mixture (in the form of a wet sheet) through the screen. After sufficient liquid has drained, the wet sheet generally can be removed from the mold and dried by pressing, heating, or a combination of the two. Generally pressures are in a range of about 300 to about 600 kPa. Temperatures in a range of 90° C. to 200° C., in a range of 100° C. to 175° C., in a range of 100° C. to 150° C., or in a range of 90° C. to 120° C. can be used for drying the wet sheet. Drying often removes all or most of the dispersing liquid (for example, up to 85 weight percent, up to 90 weight percent, up to 95 weight percent, up to 98 weight percent, or up to 99 weight percent of the dispersing liquid based on the amount of dispersing liquid added to form the dispersion). The applied heat can be used to melt the polymeric binder fibers.

The resulting porous device is a dry sheet having an average thickness of at least 0.1 millimeter, at least 0.2 millimeters, at least 0.5 millimeters, at least 0.8 millimeters, at least 1 millimeter, at least 2 millimeters, at least 4 millimeters, or at least 5 millimeters. The average thickness is often up to 20 millimeters, up to 15 millimeters, up to 12 millimeters, or up to 10 millimeters. Calendering can be used to provide additional pressing or fusing, if desired, of the dry sheet.

In the porous device, the microorganism-binding particles can be entrapped in the fibrous porous matrix through either chemical interactions (for example, chemical bonding) or physical interactions (for example, adsorption or mechanical entrapment), depending upon the nature of the fibers that are utilized. The microorganism-binding particles are often preferably distributed essentially uniformly throughout the fibrous porous matrix within the porous device.

Generally the average pore size of the dry porous device can be in a range of 0.1 to 10 micrometers, as measured by scanning electron microscopy (SEM). Void volumes in the range of 20 to 80 volume percent or in a range of 40 to 60 volume percent can be useful. The porosity of the dry porous device can be modified (increased) by using fibers of larger diameter or stiffness in the fiber mixture.

The porous device is typically flexible (for example, it can be a porous sheet rolled around a 0.75 inch (about 2 cm) diameter core). The uncalendered porous sheet can be cut to a desired size. In certain embodiments, the device further comprises a substrate laminated to a major surface of the particle-containing porous fibrous nonwoven matrix. The substrate can provide a convenient location on the porous device for a user to grasp the device, and optionally comprises a sheet or an applicator. For instance, a suitable sheet would be a woven or nonwoven fibrous sheet. A suitable application is wand-shaped, with the porous device attached at one end of the applicator.

In certain embodiments, one or more agents are disposed on or in the porous device to provide further beneficial effects to the skin or wound area. For example, the porous device may further comprise a therapeutic agent, an organoleptic agent, a growth factor, an analgesic, a tissue scaffolding agent, a haemostatic agent, collagen, an anesthetic, an anti-inflammatory agent, a vasodilation substance, a wound healing agent, an angiogenic agent, an angiostatic agent, an immune boosting agent, a skin sealing agent, an agent to impart bactericidal or bacteriostatic activity, an electron transfer agent to destabilize or destroy the metabolic action of microbes or biofilm formation, or combinations thereof. One suitable anti-inflammatory agent comprises a combination of a potassium salt, a zinc salt, a calcium salt, and a rubidium salt, which is a combination of salts typically found in willow bark extract.

In many embodiments, the porous device is sterile. The porous device can be sterilized (for example, by controlled heat, ethylene oxide gas, or radiation) prior to use, in order to reduce or prevent any contamination of the skin or wound during debridement.

In a second aspect, a kit is provided. The kit includes (a) a sterile package and (b) at least one (porous) device according to the first aspect, disposed in the sterile package. Each of the at least one porous devices is typically individually contained in a sterile package, such as a sealed pouch comprising foil (and/or other very low moisture vapor transmission rate materials), so that only one porous device is exposed to the atmosphere at a time when opening the sterile package. Packages may be sterilized according to known procedures (e.g., with ethylene oxide gas, steam, gamma irradiation, electron beam irradiation, hydrogen peroxide, peracetic acid, hydro-alcoholic solutions, bleach, and combinations thereof). The kit optionally includes a plurality of sterile packages each containing one porous device. Usually, the kit further includes instructions for wiping a wound or an area of skin with the at least one device. The instructions can include, for instance, suggested techniques, wiping time, etc., for debridement of a wound or an area of skin with the porous device.

In a third aspect, a method of debridement is provided. The method includes (a) providing a device comprising a particle-containing porous fibrous nonwoven matrix and (b) wiping a wound or an area of skin with the device. The particle-containing porous fibrous nonwoven matrix comprises (i) a porous fibrous nonwoven matrix comprising first polyolefin fibers, second polyolefin fibers comprising poly(ethylene), and fiberglass fibers; and (ii) a plurality of microorganism-binding particles; wherein the particles are enmeshed in the porous fibrous nonwoven matrix.

Optionally, the method further comprises adding a fluid to the particle-containing porous fibrous nonwoven matrix before the wiping, and/or the device further comprises a fluid absorbed in the particle-containing porous fibrous nonwoven matrix. The microorganism-binding particles are the same as those described above and can be prepared using the methods described above. Any suitable method can be used to distribute the microorganism-binding particle throughout the fibrous porous matrix. In many embodiments, the microorganism-binding particles are enmeshed within the fibrous porous matrix.

In a fourth aspect, another method of debridement is provided. The method includes (a) providing a device including a porous fibrous nonwoven matrix and (b) wiping a wound with the device. The device includes a porous fibrous nonwoven matrix. The porous fibrous nonwoven matrix includes first polyolefin fibers, second polyolefin fibers comprising poly(ethylene), and fiberglass fibers.

It has been discovered that porous devices according to the present disclosure are suitable not only for debridement of dry skin and wounds, but also often reducing the amount of microorganisms on the wound or on the area of skin that has been debrided. For example, the wiping with the porous device often provides at least a 2.0 log reduction in an amount of microorganisms on the wound or on the area of skin, or at least a 3.0 log reduction, or at least a 4.0 log reduction, and up to a 2.5 log reduction, or up to a 3.5 log reduction, or up to a 4.5 log reduction, or even up to a 5.5 log reduction in an amount of microorganisms on the wound or on the area of skin.

A variety of microorganisms can be captured using the porous devices described herein. The microorganisms can be, for example, bacteria (including both gram-negative bacteria and gram positive bacteria), fungi, yeasts, molds, protozoans, viruses (including both non-enveloped and enveloped viruses), bacterial endospores (for example, *Bacillus* (including *Bacillus anthracia, Bacillus cereus*, and *Bacillus subtilis*) and *Clostridium* (including *Clostridium botulinum, Clostridium difficile*, and *Clostridium perfringens*)), and combinations thereof.

Genera of microorganisms to be removed include, but are not limited to, *Escherichia, Staphylococcus, Pseudomonas*, and combinations thereof. Specific microorganism strains that can be removed include *Escherichia coli, Staphylococcus aureus, Pseudomonas aeruginosa*, and the like, and combinations thereof.

In a fifth aspect, another kit is provided. The kit includes (a) a sterile package; (b) at least one device disposed in the sterile package; and (c) instructions for wiping a wound with the at least one device. The device includes (a) a porous fibrous nonwoven matrix including first polyolefin fibers, second polyolefin fibers comprising poly(ethylene), and fiberglass fibers. The device further includes (b) a fluid absorbed in the porous fibrous nonwoven matrix.

Various embodiments are provided that include a porous device, a kit, and a method of debridement.

Embodiment 1 is a device that includes (a) a particle-containing porous fibrous nonwoven matrix including (i) a porous fibrous nonwoven and (ii) a plurality of microorganism-binding particles. The matrix includes first polyolefin fibers, second polyolefin fibers comprising poly(ethylene), and fiberglass fibers. The particles are enmeshed in the porous fibrous nonwoven matrix. The device further includes (b) a fluid absorbed in the particle-containing porous fibrous nonwoven matrix.

Embodiment 2 is the device of embodiment 1 wherein the fluid is present in an amount of at least 0.25 grams per gram of the particle-containing porous fibrous nonwoven matrix.

Embodiment 3 is the device of embodiment 1 or embodiment 2 wherein the fluid is present in an amount of at least 0.5 grams per gram of the particle-containing porous fibrous nonwoven matrix.

Embodiment 4 is the device of any of embodiments 1 to 3 wherein the fluid is present in an amount from 0.25 to 5.0 grams per gram of the particle-containing porous fibrous nonwoven matrix.

Embodiment 5 is the device of any of embodiments 1 to 4 wherein the fluid is present in an amount from 0.5 to 4.0 grams per gram of the particle-containing porous fibrous nonwoven matrix.

Embodiment 6 is the device of any of embodiments 1 to 5 wherein the microorganism-binding particles include particles selected from the group consisting of amorphous metal silicates, guanidine-functionalized metal silicates, diatomaceous earth, surface-modified diatomaceous earth, gamma-FeO(OH), metal carbonates, metal phosphates, silica, and combinations thereof.

Embodiment 7 is the device of any of embodiments 1 to 6 wherein the microorganism-binding particles include particles of amorphous metal silicates, guanidine-functionalized metal silicates, diatomaceous earth, surface-modified diatomaceous earth, gamma-FeO(OH), or combinations thereof.

Embodiment 8 is the device of embodiment 7 wherein the microorganism-binding particles include particles of amorphous, spheroidized metal silicates.

Embodiment 9 is the device of embodiment 7 or embodiment 8 wherein the microorganism-binding particles include particles of amorphous, spheroidized magnesium silicate.

Embodiment 10 is the device of embodiment 7 or embodiment 8 wherein the microorganism-binding particles include particles of amorphous, spheroidized aluminum silicate.

Embodiment 11 is the device of any of embodiments 1 to 6 wherein the microorganism-binding particles include particles of guanidine-functionalized metal silicates.

Embodiment 12 is the device of embodiment 11 wherein the microorganism-binding particles include particles of guanidine-functionalized magnesium silicate.

Embodiment 13 is the device of embodiment 11 wherein the microorganism-binding particles include particles of guanidine-functionalized aluminum silicate.

Embodiment 14 is the device of any of embodiments 1 to 6 wherein the microorganism-binding particles include particles of diatomaceous earth.

Embodiment 15 is the device of any of embodiments 1 to 6 wherein the microorganism-binding particles include particles of surface-modified diatomaceous earth.

Embodiment 16 is the device of embodiment 15 wherein the surface-modified diatomaceous earth includes diatomaceous earth bearing, on at least a portion of its surface, a surface treatment comprising titanium dioxide, ferric oxide, fine-nanoscale gold or platinum, or a combination thereof.

Embodiment 17 is the device of any of embodiments 1 to 6 wherein the microorganism-binding particles include particles of gamma-FeO(OH).

Embodiment 18 is the device of any of embodiments 1 to 17 wherein the particles are microparticles.

Embodiment 19 is the device of any of embodiments 1 to 18 wherein the first polyolefin fibers include poly(ethylene) fibers.

Embodiment 20 is the device of any of embodiments 1 to 19 wherein the second polyolefin fibers include bi-component polymeric fibers having a core-sheath structure, a side-by-side structure, an islands-in-the-sea structure, or a segmented-pie structure.

Embodiment 21 is the device of any of embodiments 1 to 20 wherein the porous fibrous nonwoven matrix further includes nylon fibers.

Embodiment 22 is the device of any of embodiments 1 to 21 wherein the porous fibrous nonwoven matrix further includes polylactic acid fibers.

Embodiment 23 is the device of any of embodiments 1 to 22 wherein the porous fibrous nonwoven matrix includes at least one fibrillated fiber.

Embodiment 24 is the device of any of embodiments 1 to 23 wherein the particle-containing porous fibrous nonwoven matrix is formed by a wetlaid process.

Embodiment 25 is the device of any of embodiments 1 to 24 wherein the device further includes a substrate laminated to a major surface of the particle-containing porous fibrous nonwoven matrix.

Embodiment 26 is the device of embodiment 25 wherein the substrate includes a sheet or an applicator.

Embodiment 27 is the device of any of embodiments 1 to 26 wherein the fluid includes water, a buffer solution, a cleansing solution, an analgesic solution, or an antimicrobial solution.

Embodiment 28 is the device of any of embodiments 1 to 27 further including a therapeutic agent, an organoleptic agent, a growth factor, an analgesic, a tissue scaffolding agent, a haemostatic agent, collagen, an anesthetic, an anti-inflammatory agent, a vasodilation substance, a wound healing agent, an angiogenic agent, an angiostatic agent, an immune boosting agent, a skin sealing agent, an agent to impart bactericidal or bacteriostatic activity, an electron transfer agent to destabilize or destroy the metabolic action of microbes or biofilm formation, or combinations thereof.

Embodiment 29 is the device of embodiment 28, wherein the anti-inflammatory agent includes a combination of a potassium salt, a zinc salt, a calcium salt, and a rubidium salt.

Embodiment 30 is the device of any of embodiments 1 to 29 wherein the device is sterile.

Embodiment 31 is a kit including (a) a sterile package and (b) at least one device of any of claims 1 to 30 disposed in the sterile package.

Embodiment 32 is the kit of embodiment 31 further including (c) instructions for wiping a wound or an area of skin with the at least one device.

Embodiment 33 is a method of debridement. The method includes (a) providing a device including a particle-containing porous fibrous nonwoven matrix and (b) wiping a wound or an area of skin with the device. The device includes (i) a porous fibrous nonwoven matrix and (ii) a plurality of microorganism-binding particles enmeshed in the porous fibrous nonwoven matrix. The porous fibrous nonwoven matrix includes first polyolefin fibers, second polyolefin fibers comprising poly(ethylene), and fiberglass fibers.

Embodiment 34 is the method of embodiment 33 wherein the method further includes adding a fluid to the particle-containing porous fibrous nonwoven matrix before the wiping.

Embodiment 35 is the method of embodiment 33 wherein the device further includes a fluid absorbed in the particle-containing porous fibrous nonwoven matrix.

Embodiment 36 is the method of embodiment 34 or embodiment 35 wherein the fluid includes water, a buffer solution, a cleansing solution, an analgesic solution, or an antimicrobial solution.

Embodiment 37 is the method of any of embodiments 33 to 36, wherein the wiping provides at least a 2.0 log reduction in an amount of microorganisms on the wound or the area of skin.

Embodiment 38 is the method of any of embodiments 33 to 37, wherein the wiping provides at least a 3.0 log reduction in an amount of microorganisms on the wound or the area of skin.

Embodiment 39 is the method of any of embodiments 33 to 38, wherein the wiping provides at least a 4.0 log reduction in an amount of microorganisms on the wound or the area of skin.

Embodiment 40 is the method of any of embodiments 34 to 39 wherein the fluid is present in an amount of at least 0.25 grams per gram of the particle-containing porous fibrous nonwoven matrix.

Embodiment 41 is the method of any of embodiments 34 to 40 wherein the fluid is present in an amount of at least 0.5 grams per gram of the particle-containing porous fibrous nonwoven matrix.

Embodiment 42 is the method of any of embodiments 34 to 41 wherein the fluid is present in an amount from 0.25 to 5.0 grams per gram of the particle-containing porous fibrous nonwoven matrix.

Embodiment 43 is the method of any of embodiments 34 to 42 wherein the fluid is present in an amount from 0.5 to 4.0 grams per gram of the particle-containing porous fibrous nonwoven matrix.

Embodiment 44 is the method of any of embodiments 33 to 43 wherein the microorganism-binding particles include particles selected from the group consisting of amorphous metal silicates, guanidine-functionalized metal silicates, diatomaceous earth, surface-modified diatomaceous earth, gamma-FeO(OH), metal carbonates, metal phosphates, silica, and combinations thereof.

Embodiment 45 is the method of any of embodiments 33 to 44 wherein the microorganism-binding particles include particles of amorphous metal silicates, guanidine-functionalized metal silicates, diatomaceous earth, surface-modified diatomaceous earth, gamma-FeO(OH), or a combination thereof.

Embodiment 46 is the method of embodiment 45 wherein the microorganism-binding particles include particles of amorphous, spheroidized metal silicates.

Embodiment 47 is the method of embodiment 45 or embodiment 46 wherein the microorganism-binding particles include particles of amorphous, spheroidized magnesium silicate.

Embodiment 48 is the method of embodiment 45 or embodiment 46 wherein the microorganism-binding particles include particles of amorphous, spheroidized aluminum silicate.

Embodiment 49 is the method of any of embodiments 33 to 44 wherein the microorganism-binding particles include particles of guanidine-functionalized metal silicates.

Embodiment 50 is the method of embodiment 49 wherein the microorganism-binding particles include particles of guanidine-functionalized magnesium silicate.

Embodiment 51 is the method of embodiment 49 wherein the microorganism-binding particles include particles of guanidine-functionalized aluminum silicate.

Embodiment 52 is the method of any of embodiments 33 to 44 wherein the microorganism-binding particles include particles of diatomaceous earth.

Embodiment 53 is the method of any of embodiments 33 to 44 wherein the microorganism-binding particles include particles of surface-modified diatomaceous earth.

Embodiment 54 is the method of embodiment 53 wherein the surface-modified diatomaceous earth includes diatomaceous earth bearing, on at least a portion of its surface, a surface treatment comprising titanium dioxide, ferric oxide, fine-nanoscale gold or platinum, or a combination thereof.

Embodiment 55 is the method of any of embodiments 33 to 44 wherein the microorganism-binding particles include particles of gamma-FeO(OH).

Embodiment 56 is the method of any of embodiments 33 to 55 wherein the particles are microparticles.

Embodiment 57 is the method of any of embodiments 33 to 56 wherein the first polyolefin fibers include poly(ethylene) fibers.

Embodiment 58 is the method of any of embodiments 33 to 57 wherein the second polyolefin fibers include bi-component polymeric fibers having a core-sheath structure, a side-by-side structure, an islands-in-the-sea structure, or a segmented-pie structure.

Embodiment 59 is the method of any of embodiments 33 to 58 wherein the porous fibrous nonwoven matrix further includes nylon fibers.

Embodiment 60 is the method of any of embodiments 33 to 59 wherein the porous fibrous nonwoven matrix further includes polylactic acid fibers.

Embodiment 61 is the method of any of embodiments 33 to 60 wherein the porous fibrous nonwoven matrix includes at least one fibrillated fiber.

Embodiment 62 is the method of any of embodiments 33 to 61 wherein the particle-containing porous fibrous nonwoven matrix is formed by a wetlaid process.

Embodiment 63 is the method of any of embodiments 33 to 62 wherein the device further includes a substrate laminated to a major surface of the particle-containing porous fibrous nonwoven matrix.

Embodiment 64 is the method of claim 63 wherein the substrate includes a sheet or an applicator.

Embodiment 65 is the method of any of embodiments 33 to 64 wherein the device further includes a therapeutic agent, an organoleptic agent, a growth factor, an analgesic, a tissue scaffolding agent, a haemostatic agent, collagen, an anesthetic, an anti-inflammatory agent, a vasodilation substance, a wound healing agent, an angiogenic agent, an angiostatic agent, an immune boosting agent, a skin sealing agent, an agent to impart bactericidal or bacteriostatic activity, an electron transfer agent to destabilize or destroy the metabolic action of microbes or biofilm formation, or combinations thereof.

Embodiment 66 is the method of embodiment 65, wherein the anti-inflammatory agent includes a combination of a potassium salt, a zinc salt, a calcium salt, and a rubidium salt.

Embodiment 67 is the method of any of embodiments 33 to 66 wherein the device is sterile.

Embodiment 68 is a method of debridement. The method includes (a) providing a device including a porous fibrous nonwoven matrix and (b) wiping a wound with the device. The device includes a porous fibrous nonwoven matrix. The porous fibrous nonwoven matrix includes first polyolefin fibers, second polyolefin fibers comprising poly(ethylene), and fiberglass fibers.

Embodiment 69 is the method of embodiment 68 wherein the method further includes adding a fluid to the porous fibrous nonwoven matrix before the wiping.

Embodiment 70 is the method of embodiment 68 wherein the device further includes a fluid absorbed in the porous fibrous nonwoven matrix.

Embodiment 71 is the method of embodiment 69 or embodiment 70 wherein the fluid includes water, a buffer solution, a cleansing solution, an analgesic solution, or an antimicrobial solution.

Embodiment 72 is the method of any of embodiments 68 to 71, wherein the wiping provides at least a 2.0 log reduction in an amount of microorganisms on the wound.

Embodiment 73 is the method of any of embodiments 69 to 72 wherein the fluid is present in an amount of at least 0.25 grams per gram of the porous fibrous nonwoven matrix.

Embodiment 74 is the method of any of embodiments 69 to 73 wherein the fluid is present in an amount of at least 0.5 grams per gram of the porous fibrous nonwoven matrix.

Embodiment 75 is the method of any of embodiments 69 to 73 wherein the fluid is present in an amount from 0.25 to 5.0 grams per gram of the porous fibrous nonwoven matrix.

Embodiment 76 is the method of any of embodiments 69 to 74 wherein the fluid is present in an amount from 0.5 to 4.0 grams per gram of the particle-containing porous fibrous nonwoven matrix.

Embodiment 77 is the method of any of embodiments 68 to 76 wherein the first polyolefin fibers include poly(ethylene) fibers.

Embodiment 78 is the method of any of embodiments 68 to 77 wherein the second polyolefin fibers include bi-component polymeric fibers having a core-sheath structure, a side-by-side structure, an islands-in-the-sea structure, or a segmented-pie structure.

Embodiment 79 is the method of any of embodiments 68 to 78 wherein the porous fibrous nonwoven matrix further includes nylon fibers.

Embodiment 80 is the method of any of embodiments 68 to 79 wherein the porous fibrous nonwoven matrix further includes polylactic acid fibers.

Embodiment 81 is the method of any of embodiments 68 to 80 wherein the porous fibrous nonwoven matrix includes at least one fibrillated fiber.

Embodiment 82 is the method of any of embodiments 68 to 81 wherein the porous fibrous nonwoven matrix is formed by a wetlaid process.

Embodiment 83 is the method of any of embodiments 68 to 82 wherein the device further includes a substrate laminated to a major surface of the porous fibrous nonwoven matrix.

Embodiment 84 is the method of claim 83 wherein the substrate includes a sheet or an applicator.

Embodiment 85 is the method of any of embodiments 68 to 84 wherein the device further includes a therapeutic agent, an organoleptic agent, a growth factor, an analgesic, a tissue scaffolding agent, a haemostatic agent, collagen, an anesthetic, an anti-inflammatory agent, a vasodilation substance, a wound healing agent, an angiogenic agent, an angiostatic agent, an immune boosting agent, a skin sealing agent, an agent to impart bactericidal or bacteriostatic activity, an electron transfer agent to destabilize or destroy the metabolic action of microbes or biofilm formation, or combinations thereof.

Embodiment 86 is the method of embodiment 85, wherein the anti-inflammatory agent includes a combination of a potassium salt, a zinc salt, a calcium salt, and a rubidium salt.

Embodiment 87 is the method of any of embodiments 58 to 86 wherein the device is sterile.

Embodiment 88 is a kit including (a) a sterile package; (b) at least one device disposed in the sterile package; and (c) instructions for wiping a wound with the at least one device. The device includes (a) a porous fibrous nonwoven matrix including first polyolefin fibers, second polyolefin fibers comprising poly(ethylene), and fiberglass fibers. The device further includes (b) a fluid absorbed in the porous fibrous nonwoven matrix.

Examples

Unless otherwise noted, all chemicals used in the examples can be obtained from Sigma-Aldrich Corp. (Saint Louis, Mo.). Unless otherwise specified, all microbiological supplies and reagents were purchased as standard products from either Sigma-Aldrich or VWR.

| Material | Vendor |
|---|---|
| Bacterial cultures *Escherichia coli* (ATCC 51813), *Staphylococcus aureus* (ATCC 6538) | American Type Culture Collection, Manassas, VA |

| Material | Vendor |
|---|---|
| Fiber 1 - 1 denier fibrillated polyethylene fibers (FYBREL380) | MiniFIBERS, Inc.; Johnson City, TN |
| Fiber 2 - 6 denier 2 inches long chopped nylon fibers | MiniFIBERS, Inc.; Johnson City, TN |
| Fiber 3 - 2 denier bicomponent ethylene vinyl acetate/polypropylene fibers | MiniFIBERS, Inc.; Johnson City, TN |
| Fiber 4 - long glass fibers (Micro-Strand 106-475 Glass Fiberglas) Schuller Inc | Johns Mansville. Denver, CO |
| Fiber 5 - fibrillated polyethylene fibers (FYBREL620) | MiniFIBERS, Inc.; Johnson City, TN |
| Fiber 6 - 255 PET core, PP sheath high melt BICO fibers | Trevira GmBH, Bobingen, Germany |
| Fiber 7 - 253 PET core, PP sheath low melt BICO | Trevira GmBH, Bobingen, Germany |
| Fiber 8 - SHORT STUFF E380F ~0.7 mm average length, 15 microns diameter polyethylene fibers | MiniFIBERS, Inc.; Johnson City, TN |
| Fiber 9 - 1.5 denier PolyLactic Acid Fibers 3.5 mm length | MiniFIBERS, Inc.; Johnson City, TN |
| Fiber 10 - SHORT STUFF E505F ~0.9 mm average length, 15 microns diameter polyethylene fibers | MiniFIBERS, Inc.; Johnson City, TN |
| Latex Binder - AIRFLEX 600BP, 50 weight percent (wt %) solids vinyl acetate emulsion | Air Products Polymers, Allentown, PA |
| Flocculant - MP 9307 Flocculant | Midsouth Chemical Co., Inc., Riggold, LA |
| CM-111 - Amorphous spheroidized magnesium silicate: Cosmetic Microspheres (CM-111) | 3M Company, St. Paul, MN |
| Hydroxyapatite - Product # 289396 | Sigma-Aldrich Corp., Saint Louis, MO |
| Calcium Carbonate - product # CX0110-1 | EM Science, Gibbstown, NJ |
| Gamma-FeO(OH) - catalog # 17531 | Alfa Aesar, Ward Hill, MA |
| DI Water - Deionized filtered 18 megaohm water from a Milli-Q Gradient System | Millipore; Waltham, MA |
| Tryptic Soy Agar plate - DIFCO Tryptic Soy Agar, prepared at 3% according to the manufacturer's instructions | BD, Sparks MD |
| Tryptic Soy Broth - DIFCO Tryptic Soy Broth, prepared at 3% according to the manufacturer's instructions | BD, Sparks MD |
| *E. coli* plate - 3M ™ *E coli*/Coliform PETRIFILM Plate; | 3M Company, St. Paul MN |
| AC plate - 3M ™ Aerobic Count PETRIFILM Plate; | 3M Company, St. Paul, MN |
| BBL Buffer ™ Butterfield's buffer, pH 7.2 ± 0.2, monobasic potassium phosphate buffer solution (VWR Catalog Number 83008-093) | VWR, West Chester, PA |
| Fetal Bovine Serum | Sigma-Aldrich |
| Comparative Example 1 - DEBRISOFT, a nonwoven debridement article | Activa Healthcare, Ltd., Burton-upon-Trent, England |
| Comparative Example 2 - SCOTT paper towels | Kimberly-Clark, Neenah, WI |

Preparing the Magnesium Silicate Containing Fibrous Nonwoven Matrix

Examples 1 and 2

Example 1

A fiber premix was prepared first by mixing Fiber 1 with 3 liters of cold distilled water in a 4 L blender (Waring Commercial Heavy Duty Blender, Model 37BL84) at medium speed for 30 seconds. The compositions of the premixes are described in Table 1 below.

TABLE 1

Compositions of Examples 1-2

| Materials (in grams) | Example 1 | Example 2 |
|---|---|---|
| Fiber 1 | 11.0 | — |
| Fiber 2 | 3.5 | 3.0 |
| Fiber 3 | 2.5 | 2.25 |
| Fiber 4 | 2.0 | 1.75 |
| Fiber 5 | — | 11.0 |
| CM-111 | 4.0 | 4.0 |

The mixture was examined for uniform dispersion of the fibers without nits or clumps. Fibers 2-4 were added and blended for 15 seconds on low speed. Then 4.0 grams of CM-111 was added along with 1 liter of distilled water and blended at low speed for 15 seconds.

A felt was prepared using a TAPPI pad maker apparatus (Williams Apparatus (Watertown, N.Y.) that had a box measuring about 30 centimeters (~12 inches) square and 30 centimeters (~12 inches) high with a fine mesh screen at the bottom and a drain valve. On the screen a ~14 inch (36 cm)×12 inch (30 cm) piece of a polyethylene spunbond (PET Lutradur 7240 obtained from Fiberweb, Cincinnati, Ohio) was laid as a scrim on the screen. The box was filled with tap water up to a height of about 5 centimeters (cm) above the screen. The particle-containing mixture was poured into the box and the valve was opened immediately which created a vacuum that pulled the water out of the box. The resulting fibrous nonwoven felt was approximately 0.8-1.0 millimeters (mm) thick.

The fibrous nonwoven felt was transferred from the apparatus onto a 30 centimeter square sheet of blotter paper (96-pound white paper; Anchor Paper; St. Paul, Minn.). The fibrous nonwoven matrix samples were then placed in an oven (Blue M Stabil-Therm™ oven, model OV-560A2; Blue Island, Ill.) set at 110° C. for about 2 hours to remove residual water. A scanning electron micrograph (SEM) of Example 1 is provided in FIG. 1.

Example 2

Example 2 was formed using the same procedure as Example 1 except that a web containing 11 grams of Fiber 5, instead of Fiber 1, was made. A scanning electron micrograph (SEM) of Example 2 is provided in FIG. 2.

Orange Pith Removal Test

The Orange Pith Removal Test is a surrogate test for removal of slough from wound surfaces, in which the pith is a surrogate for slough and the flesh of the orange is a surrogate for wound tissue. Fresh oranges were purchased from a local grocery store (Cub Foods, St. Paul). Prior to testing, oranges were warmed for 60 minutes in a 37 degree C. incubator (VRW Orbital Shaker Incubator, from VWR). The orange was half peeled off after making cuts using an X-Acto knife (purchased from VWR, West Chester, Pa.). Fibrous nonwoven matrix samples, sized 10 cm×10 cm, were soaked in 5 milliliters (ml) DI water for about 20 seconds, then wrung out manually to remove excess water. The orange was held in one hand while the other hand held the pre-moistened sample. The sample was wiped in a clockwise motion over the peeled orange for 3 minutes to remove pith while the orange flesh remained intact. Images were taken before and 1 minute and 3 minutes after the wiping procedure. Pith removal and sample linting was noted. Pith removal was assigned a score from one to three, with one being the least pith removal and three being the most pith removal. Higher pith removal is correlated to greater debridement. Sample linting was also assigned a score from one to three, with one being the least linting and three being the most linting. Lower linting is correlated to less shedding of fibers from the sample during debridement. The results are shown in Table 2 below.

The test procedure was also performed for Comparative Examples 1 and 2. After soaking in water, Comparative Example 2 balled up and showed compromised integrity and thus was not used in further orange pith removal testing.

TABLE 2

Orange Pith Removal Test Results

| Material # | Pith removal | Linting |
| --- | --- | --- |
| Example 1 | 3 | 1 |
| Example 2 | 3 | 1 |
| Comparative Example 1 | 3 | 1 |
| Comparative Example 2 | N/A (insufficient integrity for testing) | 3 |

Bacterial Removal Procedure #1

Examples 3 and 4

A single *E. coli* (ATCC 51813, a representative Gram negative microorganism) colony from a streak plate culture on Tryptic Soy Agar plate was inoculated into a glass tube containing 5 ml Tryptic Soy Broth and incubated in a shaker incubator (INNOVA 44 from New Brunswick Scientific) for 18-20 hours at 37° C. The overnight culture containing ~1×10$^9$ colony forming units (cfus)/ml was diluted 1:100 in BBL buffer to obtain a stock of ~1×10$^7$ colony forming units (cfus)/ml. A volume of 1.9 ml was added to a 5 ml snap cap tube containing 100 microliters of fetal bovine serum (final 5% organic load in inoculum) and mixed by vortexing for 10 seconds. A 100 microliter volume was transferred onto the surface of a sterile glass slide (microscope slides purchased from VWR) and spread over about half the area of the slide with a sterile pipette tip. The glass slides were then incubated in a 37° C. incubator for 40 minutes.

Example 3

2 cm×2.5 cm pieces of CM-111-containing fibrous nonwoven matrix Example 1, pre-moistened with 200 microliters sterile BBL buffer.

Example 4

2 cm×2.5 cm pieces of CM-111-containing fibrous nonwoven matrix Example 2, pre-moistened with 100 microliters sterile BBL buffer.

Comparative Example 3

2 cm×2.5 cm pieces of Comparative Example 1, pre-moistened with 200 microliters sterile BBL buffer.

Comparative Example 4

2 cm×2.5 cm pieces of Comparative Example 2, pre-moistened with 100 microliters sterile BBL buffer. Samples were cut from a 10.5 inch (27 cm) long and 8 inch (20 cm) wide section of the paper towel, that was folded to form 8 layers, to achieve thickness about 2 mm.

Each sample was held down on a slide for 30 seconds then wiped on the glass surface for 5 passes (back and forth) for about 15-20 seconds and then discarded. Using a pair of forceps, the glass slide was transferred to a 50 ml polypropylene tube containing 20 ml of Tryptic Soy Broth. The tube was capped and mixed on maximum speed a vortex mixer (VRW Analog Vortex Mixer) for 10 seconds. The broth in the tubes was serially diluted in BBL buffer and plated in 1 ml volume on *E coli* plates. An inoculated slide, without wiping, was also processed to generate 'Recovery Control'. Plates were incubated at 37° C. for 24 hours and analyzed using a Petrifilm Plate Reader (PPR from 3M Company, St. Paul) to obtain plate counts in cfus/ml. The counts then were multiplied by 20 to scale up to 20 ml.

Bacterial Removal was calculated by using the log reduction value (LRV) formula given below:

LRV=Log cfus/ml from recovery control−Log cfus/ml recovered from wiped glass slide The bacterial removal data for *E. coli* is shown in Table 3 below.

TABLE 3

Bacterial Removal data for E. coli

| Sample | Example | Recovery Control (Log cfus/ml) | Log Reduction Value |
|---|---|---|---|
| Example 1 | Example 3 | 6.0 | 2.0 |
| Example 2 | Example 4 | 6.1 | 3.0 |
| Comparative Example 1 | Comparative Example 3 | 6.1 | 1.4 |

N = 2,
std deviation <10% unless noted

Although Comparative Example 2 could not be tested in the Orange Pith Removal Test, it was tested as a single sample for removal of E. coli. A LRV of 1.4 from the recovery control of 4.5 Log cfus/ml was observed.

Examples 5 and 6

The Bacterial Removal Procedure #1 was repeated with S. aureus (ATCC 6538) to obtain data for a representative Gram positive microorganism. In addition, Comparative Example 4 was tested. The bacterial removal data for S. aureus is shown in Table 4 below.

TABLE 4

Bacterial Removal data for S. aureus

| Sample | Example | Recovery Control (Log cfus/ml) | Log Reduction Value |
|---|---|---|---|
| Example 1 | Example 5 | 6.2 | 1.8 |
| Example 2 | Example 6 | 6.4 | 2.9 |
| Comparative Example 1 | Comparative Example 4 | 6.4 | 1.3 |

N = 2,
std deviation <10% unless noted

Although Comparative Example 2 could not be tested in the Orange Pith Removal Test, it was tested as a single sample for removal of S. aureus. A LRV of 1.1 from recovery control of 4.6 Log cfus/ml was measured.

Examples 7, 8, and 9

Preparing Fibrous Nonwoven Matrices Containing BICO Fibers

Three fiber premixes were prepared by mixing various amounts of Fiber 8, Fiber 2, Fiber 3, Fiber 4, Fiber 6 and Fiber 7 as shown in Table 5 below. The fibers were added to 3 liters of cold DI water in a 4 L blender (available from VWR, Radnor, Pa., under the trade designation "WARING COMMERCIAL HEAVY DUTY BLENDER, MODEL 37BL84") and blended at low speed for 15 seconds. The mixture was examined for uniform dispersion of the fibers without nits or clumps. The microorganism-binding particle, CM-111, was added with an additional liter of DI water and mixed at low speed for 15 seconds.

A felt was prepared using a pad maker apparatus (obtained from Williams Apparatus, Watertown, N.Y., under the trade designation "TAPPI") that had a box measuring about 30 centimeters (12 inches) square and 30 centimeters (12 inches) high with a fine mesh screen at the bottom and a drain valve. On the screen a ~14 inch (36 cm)×12 inch (30 cm) piece of a polyethylene spunbond (PET Lutradur 7240 obtained from Fiberweb, Cincinnati, Ohio) was laid as a scrim on the screen. The box was filled with tap water up to a height of about 1 centimeter above the screen. The fiber and microorganism-binding particle mixture was poured into the box and the valve was opened immediately which created a vacuum that pulled the water out of the box. The resulting fibrous nonwoven felt was approximately 0.8-1 millimeter thick.

The fibrous nonwoven felt was transferred from the apparatus onto a 20 centimeter square sheet of blotter paper (96-pound white paper, obtained from Anchor Paper, St. Paul, Minn.). The fibrous nonwoven felt was sandwiched between 2 to 4 layers of blotter paper, to blot excess water.

The pressed felt was then transferred onto a fresh sheet of blotter paper and placed in an oven (obtained from SPX Thermal Product Solutions, White Deer, Pa., under the trade designation "BLUE M STABIL-THERM OVEN, MODEL OV-560A2") set at 110° C. for about 3 hours to remove residual water and to form a particle-containing porous fibrous nonwoven matrix. A scanning electron micrograph (SEM) of Example 9 is provided in FIG. 3.

TABLE 5

Compositions of Examples 7-9

| Material (grams) | Example 7 | Example 8 | Example 9 |
|---|---|---|---|
| Fiber 8 | 5.00 | 5.00 | 5.00 |
| Fiber 2 | 0 | 0 | 0 |
| Fiber 3 | 0 | 2.26 | 2.25 |
| Fiber 4 | 1.76 | 1.76 | 1.76 |
| Fiber 6 | 5.00 | 5.00 | 5.00 |
| Fiber 7 | 3.00 | 0 | 3.00 |
| CM-111 | 4.00 | 4.01 | 5.01 |

Examples 10, 11, and 12

The Orange Pith Removal Test was performed using samples of sizes 10 cm×10 cm. The material of Example 7 stuck on the orange and disintegrated as the test was being performed. Results are shown in Table 6 below.

TABLE 6

Orange Pith Removal Test Results

| Material # | Example # | Pith removal | Linting |
|---|---|---|---|
| Example 7 | Example 10 | N/A (got stuck on orange) | 3 |
| Example 8 | Example 11 | 2 | 2 |
| Example 9 | Example 12 | 2 | 2 |

Examples 13, 14, and 15

Bacterial Removal Procedure #2

A single E. coli (ATCC 51813, a representative Gram negative microorganism) colony from a streak plate culture on Tryptic Soy Agar plate was inoculated into a glass tube containing 5 ml Tryptic Soy Broth and incubated in a shaker incubator (INNOVA 44 from New Brunswick Scientific) for 18-20 hours at 37° C. The overnight culture containing ~1×10$^9$ colony forming units (cfus)/ml was diluted 1:100 in BBL buffer to obtain a stock of ~1×10$^7$ colony forming units (cfus)/ml. A volume of 1.9 ml was added to a 5 ml snap cap tube containing 100 microliters of fetal bovine serum (final 5% organic load in inoculum) and mixed by vortexing for 10 seconds. A 100 microliter volume was transferred onto the surface of a sterile glass slide (microscope slides purchased from VWR) and spread over about half the area of the slide with a sterile pipette tip. The glass slides were then incubated at room temperature for 15 minutes. All samples were tested in 2 cm×2.5 cm pieces, pre-moistened with 100 microliters of sterile BBL buffer.

The samples were held down on the slide for 30 seconds then wiped on the glass surface for 5 passes (back and forth) for about 15-20 seconds and then discarded. Using a pair of forceps, the glass slide was transferred to a 50 ml polypropylene tube containing 20 ml of Tryptic Soy Broth. The tube was capped and mixed on maximum speed a vortex mixer (VRW Analog Vortex Mixer) for 10 seconds. The broth in the tubes was serially diluted in BBL buffer and plated in 1 ml volume on E coli plates. An inoculated slide, without wiping, was processed similarly to generate 'Recovery Control'. Plates were incubated at 37° C. for 24 hours and analyzed using a Petrifilm Plate Reader (PPR from 3M Company, St. Paul) to obtain plate counts in cfus/ml. The counts then were multiplied by 20 to scale up to 20 ml. Bacterial Removal was calculated by using the log reduction value (LRV) formula given below:

LRV=Log cfus/ml from recovery control−Log cfus/ml recovered from wiped glass slide The bacterial removal data for *E. coli* is shown in Table 7 below.

TABLE 7

Bacterial Removal data for *E. coli*

| Sample | Example | Recovery Control (Log cfus/ml) | Log Reduction Value |
|---|---|---|---|
| Example 7 | Example 13 | 5.37 | 5.37 |
| Example 8 | Example 14 | 5.37 | 5.37 |
| Example 9 | Example 15 | 5.37 | 5.37 |

N = 2, std deviation <10% unless noted

Examples 16, 17, and 18

The Bacterial Removal Procedure #2 was repeated with *S. aureus* (ATCC 6538) to obtain data for a representative Gram positive microorganism. The bacterial removal data for *S. aureus* is shown in Table 8 below.

TABLE 8

Bacterial Removal data for *S. aureus*

| Material | Example | Recovery Control (Log cfus/ml) | Log Reduction Value |
|---|---|---|---|
| Example 7 | Example 16 | 6.20 | 2.71 |
| Example 8 | Example 17 | 6.20 | 2.60 |
| Example 9 | Example 18 | 6.20 | 2.17* |

N = 2, std deviation <10% unless noted
*stdev of 34% was observed

Preparing Fibrous Nonwoven Matrices with Magnesium Silicate

Example 19

A fiber premix was prepared by mixing various amounts of fibers as shown in Table 9 below. Fiber 6 was added to 3 liters of cold DI water in a 4 L blender (available from VWR, Radnor, Pa., under the trade designation "WARING COMMERCIAL HEAVY DUTY BLENDER, MODEL 37BL84") and blended at medium speed for 30 seconds. Fibers 2, 3 and 4 were added to the blender and mixed for 15 seconds on low speed. The mixture was examined for uniform dispersion of the fibers without nits or clumps. The mixture was transferred to a stainless steel beaker and mixed with an impellar mixer (Fisher Scientific Stedfast Stirrer model SL2400, available from VWR, West Chester, Pa.) at setting 4 for 5 minutes. The latex binder was dispersed in about 25 ml of DI water, added to the premix and mixed for 2 minutes. The flocculent was likewise dispersed in about 25 ml DI water, added to the premix while blending, with an additional 25 ml DI rinse water from the beaker. The microorganism-binding particle, CM-111, was added to the premix with an additional liter of DI water and mixed at for about 15 seconds.

A felt was prepared using a pad maker apparatus (obtained from Williams Apparatus, Watertown, N.Y., under the trade designation "TAPPI") that had a box measuring about 30 centimeters (12 inches) square and 30 centimeters (12 inches) high with a fine mesh screen at the bottom and a drain valve. On the screen a ~14 inch (36 cm)×12 inch (30 cm) piece of a polyethylene spunbond (PET Lutradur 7240 obtained from Fiberweb, Cincinnati, Ohio) was laid as a scrim on the screen. The box was filled with tap water up to a height of about 1 centimeter above the screen. The fiber and particle mixture was poured into the box and the valve was opened immediately which created a vacuum that pulled the water out of the box. The resulting fibrous nonwoven felt ranged from approximately 3 millimeter thick.

The fibrous nonwoven felt was transferred from the apparatus onto a 20 centimeter square sheet of blotter paper (96-pound white paper, obtained from Anchor Paper, St. Paul, Minn.). The felt was sandwiched between 2 to 4 layers of blotter paper, and rolled with a heavy rolling pin to blot excess water. The pressed felt was then transferred onto a fresh sheet of blotter paper and placed in an oven (obtained from SPX Thermal Product Solutions, White Deer, Pa., under the trade designation "BLUE M STABIL-THERM OVEN, MODEL OV-560A2") set at 110° C. for about 3 hours to remove residual water and to form a particle-containing porous fibrous nonwoven matrix.

Example 20

A fiber premix was prepared by mixing various amounts of Fiber 10, Fiber 2, Fiber 3, and Fiber 4 as shown in Table 9 below. The fibers were added to 3 liters of cold DI water in a 4 L blender (available from VWR, Radnor, Pa., under the trade designation "WARING COMMERCIAL HEAVY DUTY BLENDER, MODEL 37BL84") and blended at low speed for 30 seconds. The mixture was examined for uniform dispersion of the fibers without nits or clumps. The microorganism-binding particle was added with an additional liter of DI water and mixed at low speed for 15 seconds.

A felt was prepared using a pad maker apparatus (obtained from Williams Apparatus, Watertown, N.Y., under the trade designation "TAPPI") that had a box measuring about 30 centimeters (12 inches) square and 30 centimeters (12 inches) high with a fine mesh screen at the bottom and a drain valve. On the screen a ~14 inch (36 cm)×12 inch (30 cm) piece of a polyethylene spunbond (PET Lutradur 7240 obtained from Fiberweb, Cincinnati, Ohio) was laid as scrim on the screen. The box was filled with tap water up to a height of about 1 centimeter above the screen. The mixture was poured into the box and the valve was opened immediately which created a vacuum that pulled the water out of the box. The resulting fibrous nonwoven felt was approximately 0.8-1 millimeter thick.

The fibrous nonwoven felt was transferred from the apparatus onto a 20 centimeter square sheet of blotter paper (96-pound white paper, obtained from Anchor Paper, St. Paul, Minn.). The fibrous nonwoven felt was sandwiched between 2 to 4 layers of blotter paper, to blot excess water. The pressed felt was then transferred onto a fresh sheet of blotter paper and placed in an oven (obtained from SPX Thermal Product Solutions, White Deer, Pa., under the trade designation "BLUE M STABIL-THERM OVEN, MODEL OV-560A2") set at 110° C. for about 3 hours to remove residual water and to form a particle-containing porous fibrous nonwoven matrix.

Example 21

Example 21 was formed using the same procedure as Example 19, except that Fiber 9 was blended in 2 liters of DI water at low speed for 15 seconds first. Fibers 1, 3 and 4 were added to the blender and mixed at low speed for 30 seconds. The sample was dried at 110° C. for 2 hours to remove residual water and to form a particle-containing porous fibrous nonwoven matrix.

Example 22

Example 22 was formed using the same procedure as Example 19, except that Fiber 9 was blended in 2 liters of DI water at low speed for 15 seconds first. Fibers 1, 3 and 4 were added to the blender and mixed at low speed for 30 seconds. The sample was dried at 110° C. for 2 hours to remove residual water and to form a particle-containing porous fibrous nonwoven matrix.

Example 23

Example 23 was formed using the same procedure as Example 19, except that instead of Fiber 6, Fiber 1 was blended first.

TABLE 9

Compositions of Examples 19-23

| Material (grams) | Example 19 | Example 20 | Example 21 | Example 22 | Example 23 |
|---|---|---|---|---|---|
| Fiber 1 | — | — | 11.00 | 11.00 | 11.00 |
| Fiber 6 | 25.31 | — | — | — | — |
| Fiber 2 | 5.06 | 3.0 | — | — | 3.2 |
| Fiber 3 | 3.80 | 2.25 | 2.38 | 2.25 | 2.35 |
| Fiber 4 | 2.95 | 1.75 | 1.83 | 1.80 | 1.75 |
| Fiber 9 | — | — | 5.00 | 3.00 | — |
| Fiber 10 | — | 11.00 | — | — | — |
| CM-111 | 8.44 | 4.00 | 4.00 | 4.30 | 4.45 |
| Latex binder | 0.31 | — | — | 0.63 | 0.57 |

Examples 24 Through 28

The Orange Pith Removal Test was performed with samples of sizes 10 cm×10 cm. Results are shown in Table 10 below.

TABLE 10

Orange Pith Removal Test Results

| Material # | Example # | Pith removal | Linting |
|---|---|---|---|
| Example 19 | Example 24 | 3 | 3 |
| Example 20 | Example 25 | 2 | 3 |
| Example 21 | Example 26 | 2 | 2 |
| Example 22 | Example 27 | 3 | 1 |
| Example 23 | Example 28 | 3 | 2 |

The Bacterial Removal Procedure #1 was performed. Results for *E. coli* removal are shown in Table 11 below.

TABLE 11

Bacterial Removal data for *E. coli*

| Material # | Example # | Recovery Control (Log cfus/ml) | Log Reduction Value |
|---|---|---|---|
| Example 19 | Example 29 | 4.50 | 2.00 |
| Example 20 | Example 30 | 5.10 | 2.70 |
| Example 21 | Example 31 | 6.00 | 2.00 |
| Example 22 | Example 32 | 6.00 | 1.40 |
| Example 23 | Example 33 | 6.10 | 1.60 |

The Bacterial Removal Procedure #1 was performed. Results for *S. aureus* removal are shown in Table 12 below.

TABLE 12

Bacterial Removal data for *S. aureus*

| Material # | Example # | Recovery Control (Log cfus/ml) | Log Reduction Value |
|---|---|---|---|
| Example 19 | Example 34 | 4.60 | 3.40 |
| Example 20 | Example 35 | 6.00 | 2.60 |
| Example 21 | Example 36 | 5.80 | 1.80 |
| Example 22 | Example 37 | 6.40 | 0.80 |
| Example 23 | Example 38 | 6.40 | 1.20 |

Fluid Measurements

Samples were cut to the sizes indicated in Table 13 below. Samples were weighed dry on a standard lab balance. Next, samples were soaked in 5 ml DI water in plastic trays for about 20 seconds. Samples were then wrung out manually to remove excess water and weighed again. Weights were recorded in grams. Grams of fluid per gram dry weight of the sample and percent fluid in the sample were calculated using the formulas given below. Fluid measurements are listed in Table 13 below.

$$\text{Grams of fluid/gram weight of dry sample} = \frac{\text{Weight of wet sample} - \text{Weight of dry sample}}{\text{Weight of dry sample}}$$

$$\% \text{ fluid in sample} = \text{Grams of fluid/gram weight of dry sample} \times 100$$

TABLE 13

Fluid measurements

| Material # | Example # | Sample size in cms | Grams of fluid/gram weight of dry sample | % Fluid in sample |
|---|---|---|---|---|
| Example 1 | Example 39 | 10 × 7 | 0.28 | 27.62 |
| Example 2 | Example 40 | 9 × 7 | 3.59 | 358.68 |

TABLE 13-continued

Fluid measurements

| Material # | Example # | Sample size in cms | Grams of fluid/gram weight of dry sample | % Fluid in sample |
|---|---|---|---|---|
| Example 7 | Example 41 | 10 × 8 | 0.63 | 62.99 |
| Example 8 | Example 42 | 10 × 8 | 1.10 | 110.44 |
| Example 9 | Example 43 | 10 × 8 | 0.26 | 26.47 |
| Example 19 | Example 44 | 10 × 8 | 1.47 | 146.70 |
| Example 20 | Example 45 | 10 × 8 | 2.88 | 287.65 |
| Example 21 | Example 46 | 10 × 8 | 0.47 | 46.87 |
| Example 22 | Example 47 | 10 × 8 | 0.29 | 28.81 |
| Example 23 | Example 48 | 10 × 8 | 0.26 | 26.07 |

Preparing Fibrous Nonwoven Matrices

Example 49

A fiber premix was prepared by mixing various amounts of fibers as shown in Table 13 below. Fiber 6 was added to 3 liters of cold DI water in a 4 L blender (available from VWR, Radnor, Pa., under the trade designation "WARING COMMERCIAL HEAVY DUTY BLENDER, MODEL 37BL84") and blended at medium speed for 30 seconds. Fibers 2, 3 and 4 were added to the blender along with 1 liter DI water and mixed for 15 seconds on low speed. The mixture was examined for uniform dispersion of the fibers without nits or clumps.

A fibrous nonwoven felt was prepared using a pad maker apparatus (obtained from Williams Apparatus, Watertown, N.Y., under the trade designation "TAPPI") that had a box measuring about 30 centimeters (12 inches) square and 30 centimeters (12 inches) high with a fine mesh screen at the bottom and a drain valve. On the screen a ~14 inch (36 cm)×12 inch (30 cm) piece of a polyethylene spunbond (PET Lutradur 7240 obtained from Fiberweb, Cincinnati, Ohio) was laid as scrim on the screen. The box was filled with tap water up to a height of about 1 centimeter above the screen. The fiber mixture was poured into the box and the valve was opened immediately which created a vacuum that pulled the water out of the box. The resulting fibrous nonwoven felt ranged from approximately 0.7-1 millimeter thick.

The fibrous nonwoven felt was transferred from the apparatus onto a 20 centimeter square sheet of blotter paper (96-pound white paper, obtained from Anchor Paper, St. Paul, Minn.). The felt was sandwiched between 2 to 4 layers of blotter paper, and rolled with a heavy rolling pin to blot excess water. The pressed felt was then transferred onto a fresh sheet of blotter paper and placed in an oven (obtained from SPX Thermal Product Solutions, White Deer, Pa., under the trade designation "BLUE M STABIL-THERM OVEN, MODEL OV-560A2") set at 110° C. for about 2 hours to remove residual water and to form a porous fibrous nonwoven matrix.

Example 50

The procedure of Example 49 was followed, except that Fiber 1 was blended in 3 liters of DI water instead of Fiber 6. The resulting fibrous nonwoven felt ranged from approximately 0.7-1 millimeter thick. The composition of the fiber mixture is shown in Table 13 below.

TABLE 13

Compositions of Examples 49-50

| Material (grams) | Example 49 | Example 50 |
|---|---|---|
| Fiber 1 | — | 11.00 |
| Fiber 5 | 11.02 | — |
| Fiber 2 | 3.01 | 3.00 |
| Fiber 3 | 2.25 | 2.25 |
| Fiber 4 | 1.74 | 1.75 |

Example 51

The Bacterial Removal Procedure #1 was performed on 2 cm×2.5 cm samples of Example 49 moistened with 200 microliters sterile BBL buffer. The *E. coli* removal data is shown in Table 14.

Example 52

The Bacterial Removal Procedure #1 was performed on samples of Example 50, except that the inoculated glass slides were incubated at room temperature for 5 minutes and the 2 cm×2.5 cm samples were moistened with 200 microliters sterile BBL buffer. The *E. coli* removal data is shown in Table 14.

TABLE 14

Bacterial Removal data for *E. coli*

| Material # | Example # | Recovery Control (Log cfus/ml) | Log Reduction Value |
|---|---|---|---|
| Example 49 | Example 51 | 6.60 | 2.59 |
| Example 50 | Example 52 | 6.10 | 1.80 |

Example 53

The Bacterial Removal Procedure #1 was performed, except that the 2 cm×2.5 cm samples were moistened with 200 microliters sterile BBL buffer. The *S aureus* removal data is shown in Table 15.

Example 54

The Bacterial Removal Procedure #1 was performed, except that the inoculated glass slides were incubated at room temperature for 5 minutes and the 2 cm×2.5 cm samples were moistened with 200 microliters sterile BBL buffer. The *S aureus* removal data is shown in Table 15.

TABLE 15

Bacterial Removal data for *S. aureus*

| Material # | Example # | Recovery Control (Log cfus/ml) | Log Reduction Value |
|---|---|---|---|
| Example 49 | Example 53 | 6.11 | 2.76 |
| Example 50 | Example 54 | 6.60 | 1.85 |

Preparing Fibrous Porous Nonwoven Matrices with Metal Carbonates and Metal Phosphates Example 55

Example 55 was formed using the same procedure as Example 20, except that Fiber 8 was used in place of Fiber 10 and the microorganism-binding particle was 10 grams of hydroxyapatite in place of CM-111. The formulation is in Table 17 below. A scanning electron micrograph (SEM) of Example 55 is provided in FIG. 4.

TABLE 17

Compositions of Examples 55-56

| Material (grams) | Example 55 | Example 56 |
|---|---|---|
| Fiber 8 | 11.00 | 11.02 |
| Fiber 2 | 3.02 | 3.02 |
| Fiber 3 | 2.25 | 2.26 |
| Fiber 4 | 1.76 | 1.75 |
| Particles | 10.03 | 10.09 |

Example 56

Example 56 was formed using the same procedure as Example 20, except that Fiber 8 was used in place of Fiber 10 and the microorganism-binding particle was 10 grams of calcium carbonate in place of CM-111. The formulation is in Table 17 above.

The Orange Pith Removal Test was performed on samples of sizes 10 cm×10 cm. Results are shown in Table 18 below.

TABLE 18

Orange Pith Removal Test Results

| Material # | Example # | Pith removal | Linting |
|---|---|---|---|
| Example 55 | Example 57 | 2 | 2 |
| Example 56 | Example 58 | 3 | 2 |

Example 59 (Prophetic Example)

Preparing Fibrous Nonwoven Matrices Containing Gamma-FeO(OH)

A fiber premix is prepared by mixing various amounts of Fiber 8, Fiber 2, Fiber 3, and Fiber 4 as shown in Table 19 below. The fibers are added to 3 liters of cold DI water in a 4 L blender (available from VWR, Radnor, Pa., under the trade designation "WARING COMMERCIAL HEAVY DUTY BLENDER, MODEL 37BL84") and blended at low speed for 30 seconds. The mixture is examined for uniform dispersion of the fibers without nits or clumps. The microorganism-binding particle (gamma FeO(OH)) is added with an additional liter of DI water and mixed at low speed for 15 seconds.

A felt is prepared using a pad maker apparatus (obtained from Williams Apparatus, Watertown, N.Y., under the trade designation "TAPPI") that has a box measuring about 30 centimeters (12 inches) square and 30 centimeters (12 inches) high with a fine mesh screen at the bottom and a drain valve. On the screen a ~14 inch (36 cm)×12 inch (30 cm) piece of a polyethylene spunbond (PET Lutradur 7240 obtained from Fiberweb, Cincinnati, Ohio) is laid as a scrim on the screen. The box is filled with tap water up to a height of about 1 centimeter above the screen. The mixture is poured into the box and the valve is opened immediately which creates a vacuum that pulls the water out of the box. The resulting fibrous nonwoven felt is approximately 0.8-1 millimeter thick.

The fibrous nonwoven felt is transferred from the apparatus onto a 20 centimeter square sheet of blotter paper (96-pound white paper, obtained from Anchor Paper, St. Paul, Minn.). The felt is sandwiched between 2 to 4 layers of blotter paper, to blot excess water. The pressed felt is then transferred onto a fresh sheet of blotter paper and placed in an oven (obtained from SPX Thermal Product Solutions, White Deer, Pa., under the trade designation "BLUE M STABIL-THERM OVEN, MODEL OV-560A2") set at 110° C. for about 3 hours to remove residual water and to form a particle-containing porous nonwoven matrix.

TABLE 19

Composition of Example 59

| Material (grams) | Example 59 |
|---|---|
| Fiber 8 | 11.00 |
| Fiber 2 | 3.00 |
| Fiber 3 | 2.25 |
| Fiber 4 | 1.75 |
| Particles | 5.00 |

What is claimed is:

1. A device comprising:
   (a) a particle-containing porous fibrous nonwoven matrix comprising:
      (i) a porous fibrous nonwoven matrix in the form of a layer of interlaid fibers comprising first polyolefin fibers, second polyolefin fibers comprising polyethylene, and fiberglass fibers; and
      (ii) a plurality of microorganism-binding particles; wherein the particles are enmeshed in the porous fibrous nonwoven matrix; and
   (b) a fluid absorbed in the particle-containing porous fibrous nonwoven matrix.

2. The device of claim 1 wherein the fluid is present in an amount of at least 0.25 grams per gram of the particle-containing porous fibrous nonwoven matrix.

3. The device of claim 1 wherein the microorganism-binding particles comprise particles selected from the group consisting of amorphous metal silicates, guanidine-functionalized metal silicates, diatomaceous earth, surface-modified diatomaceous earth, gamma-FeO(OH), metal carbonates, metal phosphates, silica, and combinations thereof.

4. The device of claim 1 wherein the second polyolefin fibers comprise bi-component polymeric fibers comprising a core-sheath structure, a side-by-side structure, an islands-in-the-sea structure, or a segmented-pie structure.

5. The device of claim 1 wherein the device further comprises a substrate laminated to a major surface of the particle-containing porous fibrous nonwoven matrix.

6. The device of claim 1 wherein the fluid comprises water, a buffer solution, a cleansing solution, an analgesic solution, or an antimicrobial solution.

7. The device of claim 1 wherein the device is sterile.

8. A kit comprising (a) a sterile package and (b) at least one device of claim 1 disposed in the sterile package.

9. A method of debridement comprising:
   (a) providing a device comprising a particle-containing porous fibrous nonwoven matrix comprising:
      (i) a porous fibrous nonwoven matrix in the form of a layer of interlaid fibers comprising first polyolefin fibers, second polyolefin fibers comprising polyethylene, and fiberglass fibers; and
      (ii) a plurality of microorganism-binding particles; wherein the particles are enmeshed in the porous fibrous nonwoven matrix; and
   (b) wiping a wound or an area of skin with the device.

10. The method of claim 9 wherein the method further comprises adding a fluid to the particle-containing porous fibrous nonwoven matrix before the wiping.

11. The method of claim 9 wherein the device further comprises a fluid absorbed in the particle-containing porous fibrous nonwoven matrix.

12. The method of claim 10 wherein the fluid comprises water, a buffer solution, a cleansing solution, an analgesic solution, or an antimicrobial solution.

13. The method of claim 9 wherein the wiping provides at least a 2.0 log reduction in an amount of microorganisms on the wound or the area of skin.

14. The method of claim 9 wherein the microorganism-binding particles comprise particles comprise particles of amorphous metal silicates, guanidine-functionalized metal silicates, diatomaceous earth, surface-modified diatomaceous earth, gamma-FeO(OH), or a combination thereof.

\* \* \* \* \*

UNITED STATES PATENT AND TRADEMARK OFFICE
CERTIFICATE OF CORRECTION

Page 1 of 2

PATENT NO. : 10,709,807 B2
APPLICATION NO. : 15/509501
DATED : July 14, 2020
INVENTOR(S) : Manjiri Kshirsagar It is certified that error appears in the above-identified patent and that said Letters Patent is hereby corrected as shown below:

On the Title Page

Item (74) Under Attorney, Agent, or Firm, delete "Andrian L. Pishko" and insert -- Adrian L. Pishko --, therefor.

Second Page, Column 2,
Item (56) Under Other Publications, delete "pGES." and insert -- pages. --, therefor.

In the Specification

Column 4,
Line 7, delete "poly(l-" and insert -- poly(1- --, therefor.

Column 15,
Line 10, delete "anthracia," and insert -- anthracis, --, therefor.

In the Claims

Column 34,
Line 35, in Claim 2, delete "claim 1" and insert -- claim 1, --, therefor.
Line 38, in Claim 3, delete "claim 1" and insert -- claim 1, --, therefor.
Line 44, in Claim 4, delete "claim 1" and insert -- claim 1, --, therefor.
Line 48, in Claim 5, delete "claim 1" and insert -- claim 1, --, therefor.
Line 51, in Claim 6, delete "claim 1" and insert -- claim 1, --, therefor.
Line 54, in Claim 7, delete "claim 1" and insert -- claim 1, --, therefor.

Column 35,
Line 1, in Claim 10, delete "claim 9" and insert -- claim 9, --, therefor.
Line 4, in Claim 11, delete "claim 9" and insert -- claim 9, --, therefor.
Line 7, in Claim 12, delete "claim 10" and insert -- claim 10, --, therefor.

Signed and Sealed this
Third Day of November, 2020

Andrei Iancu
*Director of the United States Patent and Trademark Office*

CERTIFICATE OF CORRECTION (continued)
U.S. Pat. No. 10,709,807 B2

Line 10, in Claim 13, delete "claim 9" and insert -- claim 9, --, therefor.
Line 13, in Claim 14, delete "claim 9" and insert -- claim 9, --, therefor.
Line 14, in Claim 14, delete "particles comprise particles comprise" and insert -- particles comprise --, therefor.